(12) United States Patent
Daulton et al.

(10) Patent No.: US 11,133,086 B2
(45) Date of Patent: Sep. 28, 2021

(54) METHODS, SYSTEMS AND COMPUTER PROGRAM PRODUCTS FOR CHEMICAL HAZARD EVALUATION

(71) Applicants: Daniel J. Daulton, The Woodlands, TX (US); Jo Ann McMahon, Arnold, MO (US); William J. Kuc, St. Louis, MO (US); Charles Lee Ake, Jr., St. Louis, MO (US); Denise Hill, Houston, TX (US); Thomas Grumbles, Cypress, TX (US)

(72) Inventors: Daniel J. Daulton, The Woodlands, TX (US); Jo Ann McMahon, Arnold, MO (US); William J. Kuc, St. Louis, MO (US); Charles Lee Ake, Jr., St. Louis, MO (US); Denise Hill, Houston, TX (US); Thomas Grumbles, Cypress, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 894 days.

(21) Appl. No.: 15/210,159

(22) Filed: Jul. 14, 2016

(65) Prior Publication Data

US 2016/0321433 A1     Nov. 3, 2016

Related U.S. Application Data

(63) Continuation of application No. 14/048,188, filed on Oct. 8, 2013, now Pat. No. 9,424,517.

(51) Int. Cl.
*G06F 17/00* (2019.01)
*G06Q 50/02* (2012.01)
(Continued)

(52) U.S. Cl.
CPC ............... *G16C 20/30* (2019.02); *G06N 5/04* (2013.01); *G06Q 10/10* (2013.01); *G06Q 50/26* (2013.01)

(58) Field of Classification Search
CPC .......... G16C 20/30; G06N 5/04; G06Q 10/10; G06Q 50/26
(Continued)

(56) References Cited

U.S. PATENT DOCUMENTS

| 6,097,995 A | 8/2000 | Tipton et al. |
| 6,397,115 B1 | 5/2002 | Basden |

(Continued)

OTHER PUBLICATIONS

Thatcher et al ; "Impact of the OSPAR Decision on the Harmonized Mandatory Control Scheme on the Offshore Chemical Supply Industry"; Oct. 2001 ; pp. 1-12.*
(Continued)

*Primary Examiner* — Brandon S Cole
(74) *Attorney, Agent, or Firm* — Cantor Colburn LLP

(57) ABSTRACT

A method of assessing chemical products includes: receiving input data including identification of a chemical substance at a processing device; evaluating a regulatory impact of the chemical substance based on at least one of global regulation data, regional regulation data and jurisdiction-specific regulation data, and outputting a regulatory impact assessment; evaluating potential hazards posed by the chemical substance based on available data related to characteristics of the chemical substance by comparing the characteristics to a plurality of criteria including environmental criteria, toxicity criteria related to effects on human health, and physical criteria related to hazards encountered during material transportation and handling, and outputting a chemical hazard assessment; and generating a chemical assessment report indicating potential impact due to use of the chemical substance, the chemical assessment report indicating chemi-
(Continued)

cal assessment results that include the regulatory impact assessment and the chemical hazard assessment.

18 Claims, 22 Drawing Sheets

(51) Int. Cl.
    *G06Q 10/10*     (2012.01)
    *G16C 20/30*     (2019.01)
    *G06N 5/04*     (2006.01)
    *G06Q 50/26*     (2012.01)

(58) Field of Classification Search
    USPC ........................................................ 706/1–62
    See application file for complete search history.

(56) References Cited

U.S. PATENT DOCUMENTS

| | | | |
|---|---|---|---|
| 6,441,743 | B1 | 8/2002 | Berger |
| 6,973,362 | B2 | 12/2005 | Long et al. |
| 7,171,426 | B2 | 1/2007 | Farmer et al. |
| 7,542,884 | B2 | 6/2009 | Boris et al. |
| 9,424,517 | B2 * | 8/2016 | Daulton .................. G06Q 10/10 |
| 9,799,006 | B2 * | 10/2017 | Daulton .................. G06Q 10/10 |
| 2002/0192671 | A1 | 12/2002 | Castle et al. |
| 2004/0083060 | A1 | 4/2004 | Church et al. |
| 2004/0138826 | A1 | 7/2004 | Carter, Jr. et al. |
| 2007/0005264 | A1 | 1/2007 | Singh et al. |
| 2007/0217129 | A1 | 11/2007 | Wang et al. |
| 2007/0271299 | A1 * | 11/2007 | Wang ...................... G06Q 10/00 |
| 2010/0023359 | A1 | 1/2010 | Easo et al. |
| 2010/0318371 | A1 * | 12/2010 | Sanders, Jr. ........ G06Q 30/0282 |
| | | | 705/1.1 |
| 2011/0246397 | A1 | 10/2011 | Predale et al. |
| 2012/0173444 | A1 | 7/2012 | Zik et al. |
| 2015/0100248 | A1 | 4/2015 | Daulton et al. |
| 2015/0100533 | A1 | 4/2015 | Daulton et al. |
| 2016/0063375 | A1 * | 3/2016 | Gilgert ................. G06Q 30/018 |
| | | | 706/46 |

OTHER PUBLICATIONS

"Using Chemical Hazard Assessment for Alternative Chemical Assessment and Prioritization"; Outdoor Industry Association Chemicals Managment Working Group & the Zero Discharge of Hazardous Chemicals Programme; Draft Document: Ver 1, Mar. 2013; 30 pgs.

Andersen, "Toxicokinetic modeling and its applications in chemical risk assessment", M.E. Andersen / Toxicology Letters 138 (2003), pp. 9-27.

Cowan-Ellsberry, "Modeling Exposure to Persistent Chemicals in Hazard and Risk Assessment," SETAC Journal, Lawrence Berkeley National Laboratory, Feb. 9, 2010, 66 pages.

Daulton et al., "Global Chemical Evaluation Process Review to Qualify Regulatory and Environmental Characteristics for Oilfield Chemical Products", SPE 159690, SPE Annual Technical Conference and Exhibition, San Antonio, TX, Oct. 8-10, 2012, 12 pages.

Echa, "Chemical Safety Assessment", 2009, 22 pages; http://europa.eu.

Ellis et al., "Evaluation of a Gradient Sampling Design Forenvironmental Impact Assessment", Environmental Monitoring and Assessment 48: pp. 157-172, 1997. 1997 Kluwer Academic Publishers. Printed in the Netherlands.

Evans, "Decision Analysis for Integrated Reservoir Management", SPE European Petroleum Conference held in Paris, France, Oct. 24-25, 2000, 6 pages.

Grini et al., Choosing Produce dWater Treatment Technologies Based on Environmental Impact Reduction, SPE 74002, SPE International Conference on Health, Safety and Environment in Oil and Gas Exploration, Kuala Lumpur, Malaysia, Mar. 20-22, 2002, 11 pages.

Jordan et al, "Quantitative Ranking Measures Oil Field Chemicals EnvironmentalImpact", SPE Annual Technical Conference and Exhibition held in Florence, Italy, Sep. 19-22, 2010, 9 pages.

Knudsen et al., "Toward Zero Environmental Impact of the Produced Water", Offshore Europe 2003, Aberdeen, UK, Sep. 2-5, 2003, 6 pages.

McLean et al., "A Method for Improving Chemical Product Risk Profiles as Part of Product Development", SPE 159355, SPE Annual Technical Conference and exhibition, San Antonio, Texas, USA, Oct. 8-10, 2012, 12 pages.

Sanders et al., "Are your Chemical Products Green—A Chemical Hazard Scoring System", SPE 126451, SPE International Conference on Health, Safety, and Environment in Oil and Gas Exploration and Production, Rio de Janeiro, Brazil, Apr. 12-14, 2010, 6 pp.

Still, et al., The Development and Introduction of Chemical Hazard Assessment and Risk Management (CHARM) into the Regulation of Offshore Chemicals . . . Warning to Industry for the Future?; 2002: Special Publication—Royal Society of Chemistry 280; pp. 31-43.

Swanson, et al., "A Screening Method for Ranking and Scoring Chemicals by Potential Human Health and Environmental Impacts", ETC, 1997,pp. 372-383.

Thatcher, et al., "Impact of the OSPAR Decision on the Harmonized Mandatory Control Scheme on the Offshore Chemical Supply Industry"; Oct. 2001; pp. 1-12.

* cited by examiner

Product Name: XYZ

Highly Discouraged Substances

The following substances are HIGHLY DISCOURAGED from being intentionally added, at any concentration, to Fluids and Chemical Products. Inclusion in a product will require justification and/or management approval.

| United Nations Environment Programme Persistent Organic Pollutants | |
|---|---|
| Substance | CASRN |
| ALDRIN | 309-00-2 |
| CHLORDANE | 57-74-9 |
| DDT | 50-29-3 |
| DIELDRIN | 60-57-1 |
| DIOXINS and FURANS | various |
| ENDRIN | 72-20-8 |
| HEXACHLOROBENZENE | 118-74-1 |
| HEPTACHLOR | 76-44-8 |
| MIREX | 2385-85-5 |
| POLYCHLORINATED BIPHENY | 1336-36-3 |
| TOXAPHENE | 8001-35-2 |

| EPA Priority Persistent Bioaccumulative & Toxic Chemicals | |
|---|---|
| Substance | CASRN |
| ALDRIN | 309-00-2 |
| ALKYL-LEAD compounds | various |
| BENZO[a]PYRENE | 50-32-8 |
| CHLORDANE | 57-74-9 |
| DIELDRIN | 60-57-1 |
| DIOXINS and FURANS | various |
| DDT and metabolites DDD & DDE | various |
| HEXACHLOROBENZENE | 118-74-1 |
| MERCURY elemental and compound | various |
| MIREX | 2385-85-5 |
| OCTACHLOROSTYRENE | 29082-74-4 |
| POLYCHLORINATED BIPHENYLS | 1336-36-3 |
| TOXAPHENE | 8001-35-2 |

FIG.4

| Substance Letter Identifier: | A | B | C | D | E | F | G | H |
|---|---|---|---|---|---|---|---|---|
| Substance Name: | Subs A | Subs B | Subs C | Subs D | Subs E | Subs F | Subs G | Subs H |
| CAS Number: | ###-##-#### | ###-##-#### | ###-##-#### | ###-##-#### | ###-##-#### | ###-##-#### | ###-##-#### | ###-##-#### |
| Percent Compostion: | 0.00% | 0.00% | 0.00% | 0.00% | 0.00% | 0.00% | 0.00% | 0.00% |
| Substance Totals for Lists "Present On" | 0 | 0 | 0 | 0 | 0 | 0 | 0 | 0 |
| European Commission CLP Hazard phrases | Mark Only "Harmonized" H-Phrases here | | | | | | | |
| H340 or H341 May Cause or Suspected of Causing Genetic Defects | | | | | | | | |
| H350 or H351 May Cause or Suspected of Causing Cancer | | | | | | | | |
| H360 or H361 May Damage or Suspected of Damaging fertility or the unborn child | | | | | | | | |
| Globally Applicable Regulatory Lists | | | | | | | | |
| US Department of Transportation Marine Pollutants | | | | | | | | |
| National Toxicology Program – Carcinogens | | | | | | | | |
| International Agency for Research on Cancer – Carcinogens | | | | | | | | |

FIG.5

| | | | | | | | | | | |
|---|---|---|---|---|---|---|---|---|---|---|
| UN Environment Programme Banned Chemicals | EUROPA Annex 13 Category 1 Endocrine Disruptors | Eastern Hemisphere Regulatory Lists | European Chemicals Agency Substances of Very High Concern | European Commission Priority Substances & Certain Other Pollutants | OSPAR Chemicals for Priority Action | Australia Air Toxics Program – Priority Pollutants | Australian Drinking Water Guidelines (2011) | Australia National Pollutant Inventory Guide to Reporting | ERMA New Zealand Reassessment Priority List | |

FIG.5-1

| Western Hemisphere Regulatory Lists | | | | | | | | | | | |
|---|---|---|---|---|---|---|---|---|---|---|---|
| EPA Safe Drinking Water Act Maximum Contaminant Levels | | | | | | | | | | | |
| EPA Clean Water Act Priority Pollutants | | | | | | | | | | | |
| EPA Hazardous Air Pollutants | | | | | | | | | | | |
| EPA Volatile Organic Chemicals | | | | | | | | | | | |
| EPCRA Sec. 302 Extremely Hazardous Substances | | | | | | | | | | | |
| EPCRA Sec. 313 Toxic Chemicals | | | | | | Product Totals for Lists "Present On" | | | | | |
| US DOT Environmentally Hazardous Chemicals | | | | | | Global | Eastern Hemisphere | Western Hemisphere | Number of Individual Lists | | |
| FDA GRAS List | | | | | | 0 | 0 | 0 | 0 | | |
| Environment Canada – Acts & Regulations – Toxic Substances List – Schedule 1 | | | | | | | | | | | |
| Environment Canada – Acts & Regulations – Priority Substances List | | | | | | | | | | | |

FIG.5-2

| Decision Tree for Performing Pre-Screen Prediction | |
|---|---|
| I. | |
| Is the substance inorganic? | Y/N? |
| I.i. | |
| If yes, to I. then is LC50/EC50 < 1 ppm? | Y/N? |
| If No to I. (substance is organic), proceed to II. | |
| I.i.a. | |
| If Yes to I.i., then Fail Pre-Screen | |
| II. | |
| Is biodeg <20% for OECD 306 or Marine Bodis, or other marine protocols, or <20% in OECD 301 or OECD 310? | Y/N? |
| II.i. | |
| If Yes to II. Then Fail Pre-Screen If No to II., proceed to III. | |
| III. | |
| Does the substance meet 2 out the 3 following criteria? | |
| III.i. Biodegradation OR | |
| Is Biodeg < 60% in OECD 306, or Marine Bodis, or OECD 301B, or 301C, or 301D, or 301F, or 310, or Freshwater Bodis or <70% in OECD 301A or 301E? | Y/N? |
| III.ii. Bioaccumulation OR | |
| Is BCF > 100 or (log Pow $\geq$3 and molecular weight <700)? | Y/N? |
| III.iii. Toxicity OR | |
| Is aquatic toxicity LC50 or EC50 values <10 ppm? | Y/N? |
| If Yes to III., Then Fail Pre-Screen If No to III., then Pass Pre-Screen | |

FIG.6

| Product Name: XYZ | CEPR Workbook OSPAR Pre-Screen Prediction | | | | | |
|---|---|---|---|---|---|---|
| Substance Letter Identifier: | A | B | C | D | E | F |
| Substance Name: | Subs A | Subs B | Subs C | Subs D | Subs E | Subs F |
| CAS Number: | ###-##-#### | ###-##-#### | ###-##-#### | ###-##-#### | ###-##-#### | ###-##-#### |
| Percent Composition: | 0.00% | 0.00% | 0.00% | 0.00% | 0.00% | 0.00% |
| BIODEGRADATION | | | | | | |
| Value #1 (%) | | | | | | |
| Method #1 | | | | | | |
| Value #2 (%) | | | | | | |
| Method #2 | | | | | | |
| Value #3 (%) | | | | | | |
| Method #3 | | | | | | |
| BIOACCUMULATION | | | | | | |
| BCF value | | | | | | |
| Test Method | | | | | | |
| log(Pow) value | | | | | | |
| Test Method | | | | | | |
| Molecular Weight | | | | | | |
| AQUATIC TOXICITY | | | | | | |
| EC50 or LC50 value #1 (ppm) | | | | | | |
| Aquatic specie #1 | | | | | | |
| Test Method #1 | | | | | | |

FIG.7

| EC50 or LC50 value #2 (ppm) | Aquatic specie #2 | Test Method #2 | EC50 or LC50 value #3 (ppm) | Aquatic specie #3 | Test Method #3 | SUBSTANCE RESULTS | PRODUCT RESULT |
|---|---|---|---|---|---|---|---|
| | | | | | | | |
| | | | | | | | |
| | | | | | | | |
| | | | | | | | |
| | | | | | | | |
| | | | | | | | |

FIG.7-1

| Product Name: XYZ | | | | | | | |
|---|---|---|---|---|---|---|---|
| | Substance Letter Identifier: | A | B | C | D | E | F |
| | Substance Name: | Subs A | Subs B | Subs C | Subs D | Subs E | Subs F |
| | CAS Number: | ###-##-#### | ###-##-#### | ###-##-#### | ###-##-#### | ###-##-#### | ###-##-#### |
| | Composition: | 0.00% | 0.00% | 0.00% | 0.00% | 0.00% | 0.00% |
| Environmental Hazards | | | | | | | |
| Acute Aquatic Toxicity | | | | | | | |
| Bioaccumulation | | | | | | | |
| Biodegradation | | | | | | | |
| Total Score/Component | | 0 | 0 | 0 | 0 | 0 | 0 |
| Toxicological Hazards | | | | | | | |
| Acute Mammalian Toxicity | | | | | | | |
| Carcinogenicity | | | | | | | |
| Mutagenicity | | | | | | | |
| Reproductive and Developmental | | | | | | | |
| Eye & Skin Corrosive/Irritant | | | | | | | |
| Total Score/Component | | 0 | 0 | 0 | 0 | 0 | 0 |

CEPR Workbook Chemical Hazard Evaluation

FIG.8

| Product Name: XYZ | | Product Total Score | Product Relative Score | | | | |
|---|---|---|---|---|---|---|---|
| Physical Hazards | | 0 | 0 | | | | |
| Explosive | | out of 3400 possible points | out of 100 possible points | | | | |
| Flammable | | | | | | | |
| Oxidizer | | | | | | | |
| Metal Corrosive | | | | | | | |
| Total Phys Haz Score | 0 | | | | | | |
| Relative Phys Haz Score | 0 | | | | | | |

FIG. 8-1

CEPR Workbook Environmental Scoring Criteria

| SCORE | Environmental Criteria | | | |
|---|---|---|---|---|
| | 0 | 1 | 2 | 3 |
| CRITERIA | | | | |
| Acute Aquatic Toxicity* | ≥ 100 ppm | > 10ppm and ≤ 100ppm | > 1 ppm and ≤ 10ppm | ≤ 1ppm |
| Bioaccumulation** | BCF < 1000 or log(Kow) ≤ 4.0 or molecular weight > 700 | 2000 > BCF ≥ 1000 | 5000 > BCF ≥ 2000 or log(Kow) > 4.0 or molecular weight ≤ 700 | BCF ≥ 5000 |
| Biodegradation† | ≥ 60% and does not produce degradation products of concern | < 59% and ≥ 40% | < 39% and ≥ 20% | ≤ 19% or produces degradation products of concern |

\* Based on most conservative LC50 (fish species) or EC50 (algae and crustacea) value.
\*\* Based on REACH (2000, 5000, and US EPA 1000)
†Based on most conservative value from 28 day, OECD 301D or OECD 306 biodegradation tests.

FIG.9

CEPR Workbook Toxicity Criteria

Acute Hazards

| SCORE | 0 | 1 | 2 | 3 |
|---|---|---|---|---|
| CRITERIA | | | | |
| Acute toxicity (1 exposure route) | See criteria below | See criteria below | See criteria below | See criteria below |
| Acute toxicity (2 exposure routes) | 0-1 | 2-3 | 4-5 | 6 |
| Acute toxicity (3 exposure routes) | 0-2 | 3-5 | 6-8 | 9 |
| Carcinogenicity | See criteria below | See criteria below | See criteria below | See criteria below |
| Reproductive Toxicity (see detailed criteria below) | Negative results in all reproductive toxicity tests, or | | | Evidence from any route of exposure – doses shown below, or |
| Harmonized CLP Classification | Not Classified | | | Category 1A, 1B or 2 |
| Mutagenicity | Negative results in all mammalian in-vitro or in-vivo tests, of human epidemiological studies, or Ames test, or | Positive result in some in-vitro somatic cell tests or weight of evidence if more than one Ames test result is reported, or | Evidence for mutagenicity in mammalian germ cells, or | Positive evidence of mutagenicity from human epidemiological studies, or |
| Harmonized CLP Classification | Not Classified | Category 2 | Category 1B | Category 1A |
| Corrosive/Irritant | Non-corrosive/non-irritant, Category 1A or 1B, or appropriate qualitative descriptions below | Category 1C, or either irritant or causes permanent eye damage, or appropriate qualitative descriptions below | | |

FIG. 10A

| Possible Scores | Carcinogenicity Criteria | | | |
|---|---|---|---|---|
| | 0 | 1 | 2 | 3 |
| Harmonized CLP Classification | Not Classified, or | There is no CLP classification category that is scored as 1. | Category 1B or 2– Presumed or Suspected human carcinogen, or | Catergory 1A – Known human carcinogen, or |
| IARC Descriptors | Group 4 – Probably Not carcinogenic to humans, or | Group 3– Not Classifiable as to its carcinogenicity in humans, or | Group 2A or 2B – Probably or Possibly carcinogenic to humans, or | Group 1 – Carcinogenic to humans, or |
| NTP 12th Report on Carcinogens – Listing Criteria | No descriptive terms for this score were part of the NTP ROC classification system, or | No descriptive terms for this score were part of the NTP ROC classification system, or | Reasonably Anticipated to be a human carcinogen, or | Known to be a human carcinogen, or |
| EPA 1986 Guideline Classification System | Group E – Evidence of Non-Carcinogenicity for humans, or | Group D – Not Classifiable as to human carcinogenicity, or | Broup B1, B2 or C– Probable or Possible human carcinogen, or | Group A Human carcinogen, or |
| EPA 2005 Guideline Classification System | Not likely to be carcinogenic to humans. | Inadequate Information to assess carcinogenic potential. | a) Likely to be carcinogenic to humans or b) Suggestive evidence of carcinogenic potential. | Carcinogenic to humans. |

FIG. 10A-1

| Acute Toxicity Criteria | | | | | |
|---|---|---|---|---|---|
| Possible Scores | 0 | 1 | 2 | 3 | |
| Exposure route | Category 4 | Category 3 | Category 2 | Category 1 | |
| Oral (mg/kg bodyweight) | > 300 | > 50 and ≤ 300 | > 5 and ≤ 50 | ≤ 5 | |
| Dermal (mg/kg bodyweight) | > 1000 | >200 and ≤ 1000 | > 50 and ≤ 200 | ≤ 50 | |
| Inhalation – Gases (ppmV) | > 2500 | > 500 and ≤ 2500 | > 100 and ≤ 500 | ≤ 100 | |
| Inhalation – Vapors (mg/L) | > 10 | > 2 and ≤ 10 | > 0.5 and ≤ 2 | ≤ 0.5 | |
| Inhalation – Dusts and Mists | > 1 | > 0.5 and ≤ 1 | > 0.05 and ≤ 0.5 | ≤ 0.05 | |

Acute toxicity values are expressed as LD50 (oral, dermal) or LC50 (inhalation).

| Reproductive Effect Criteria | | |
|---|---|---|
| Possible Scores | 0 | 3 |
| Exposure route | | |
| Oral (mg/kg-bw/day) | > 250 | 0 – 250 |
| Dermal (mg/kg-bw/day) | > 200 | 0 – 200 |
| Inhalation (gas) (ppm/6h/day) | > 250 | 0 – 250 |
| Inhalation (vapor) (ppm/6h/day) | > 1 | 0 – 1 |
| Inhalation (dust/mist) (mg/L/6h/day) | > 0.2 | 0 – 0.2 |

| Skin Corrosion Criteria | | |
|---|---|---|
| Corrosive sub-categories | Corrosive in 1 of 3 animals! | |
| | Exposure | Observation |
| 1A | ≤ 3 min | ≤ 1 h |
| 1B | > 3 min ≤ 1 h | ≤ 14 days |
| 1C | > 1 h ≤ 4 h | ≤ 14 days |

FIG. 10B

Skin and Eye Irritation Effects: Quantitative Descriptions

| Skin Irritant (Score of 1) | Reversible eye effects (Score of 0) | Irreversible eye effects (Score of 1) |
|---|---|---|
| (1) Mean value of 2.3 to 4.0, inclusive, for erythema/eschar or for oedema in at least 2 of 3 tested animals from gradings at 24, 48, and 72 hours after patch removal or, if reactions are delayed, from grades on 3 consecutive days after the onset of skin reactions; or (2) Inflammation that persists to the end of the observation period normally 14 days in at least 2 animals, particularly taking into account alopecia (limited area), hyperkeratosis, hyperplasia, and scaling; or (3) In some cases where there is pronounced variability of response among animals, with very definite positive effects related to chemical exposure in a single animal but less than the criteria above. | An eye irritant Category 2A (irritating to eyes) is a substance that produces: at least in 2 of 3 tested animals a positive response of: (i) corneal opacity ≥ 1; and/or (ii) iritis ≥ 1; and/or (iii) conjunctival redness ≥ 2; and/or (iv) conjunctival edema (chemosis) ≥ 2 calculated as the mean scores following grading at 24, 48, and 72 hours after installation of the substance, and which fully reverses within an observation period of normally 21 days. | An eye irritant Category 1 (irreversible effects on the eye) is a substance that produces: (a) at least in one animal effects on the cornea, iris, or conjunctiva that are not expected to reverse or have not fully reversed within an observation period of normally 21 days; and/or (b) at least in 2 of 3 tested animals, a positive response of: (i) corneal opacity ≥ 3; and/or (ii) iritis > 1.5; calculated as the mean scores following grading at 24, 48, and 72 hours after installation of the substance. |

FIG. 10B-1

| Skin and Eye Irritation Effects: Qualitative Descriptions | | |
|---|---|---|
| Possible Scores | 0 | 1 |
| Description of Skin Effects | Essentially nonirritating, slightly to mildly irritating | Can cause moderate skin irritation, severely irritating and/or corrosive, may cause destruction to dermal tissue |
| Description of Eye Effects | Essentially nonirritating, slightly to midly irritating, reversible effects | Moderately to severely irritating, corrosive, irreversible destruction of ocular tissue |

FIG. 10B-2

| CEPR Workbook Physical Hazard Criteria | | | | |
|---|---|---|---|---|
| Physical Hazards | | | | |
| Possible Scores | 0 (also see note 1) | 1 | 2 | 3 |
| CRITERIA | | | | |
| Explosive | | | | |
| GHS Classification | Division 1.5 or Division 1.6 | Division 1.3 or Division 1.4 | Division 1.2 | Division 1.1 |
| USDOT Classification | Division 1.6 | Division 1.4 or Division 1.5 | Divisions 1.2 or Division 1.3 | Division 1.1 |
| IMDG Classification | Division 1.5 or Division 1.6 | Division 1.3 or Division 1.4 | Division 1.2 | Division 1.1 |
| Flammable Liquids | Category 4– Flash Point > 60°C (140°F) and ≤ 93°C (199.4°F) | Category 3– Flash Point ≥ 23°C (73.4°F) and ≤ 60°C (140°F) | Category 2– Flash Point < 23°C (73.4°F) and initial boiling point > 35°C (95°F) | Category 1– Flash Point < 23°C (73.4°F) and initial boiling point ≤ 35°C (95°F) |
| Corrosive | Not Classified – Corrosion rate on either steel or aluminum surfaces less than 6.25 mm per year (mpy) at a test temperature of 55°C (131°F), or | | | Category 1– Corrosion rate on either steel or aluminum surfaces greater than or equal to 6.25 mm per year (mpy) at a test temperature of 55°C (131°F), or |
| | MSDS indicates US DOT Class 8, unregulated | | | MSDS indicates US DOT Class 8, Packing Group I, II, or III |
| Oxidizer (also see note 2) | Endpoint not identified on product MSDS. | Substance identified as Class 1 oxidizer on NFPA 400/430 list. | Substance identified as Class 2 oxidizer on NFPA 400/430 list, or, Product MSDS identifies oxidizer hazard and substances are not found on NFPA list. | Substance identified as either Class 3 or Class 4 oxidizer on NFPA 400/430 list. |

Note 1: US DOT regulations require that, if one of these hazards are present, it must be designated on the product MSDS. Therefore, if any one of these endpoints is not identified on the product MSDS, it should be scored as 0.

Note 2: When a product contains multiple substances, base the assessment on the most conservative NFPA classification.

FIG. 11

CEPR RESULTS FOR HIGHLY DISCOURAGED or HIGHLY REGULATED CHEMICALS

| Chemical | CAS # | HDS* | OSPAR Pre-Screen Estimate | H- Phrases** | Total Regulatory Count | Estimated CEPR SCORE† | Comments |
|---|---|---|---|---|---|---|---|
| Aldrin | 309-00-2 | Yes | Fail | H351 | 8 | 50 | --- |
| Benzene | 71-43-2 | No | Pass | H340 H350 | 12 | 39 | Log (Pow)=2.13, readily bio-degradable |
| Benzo[a]pyrene | 50-32-8 | Yes | Fail | H340 H350 H360 | 7 | 56 | --- |
| Dibutyl Phthalate | 84-74-2 | Yes | Fail | H360 | 10 | 27 | --- |
| # 2 Diesel | 68476-34-6 | No | Fail | H351 | 7 | 39 | Regulatory count based upon presence of naphthalene |

*Highly Discouraged Substance (HDS)
**The following H phrases were considered:
- H340 May cause genetic defects
- H341 Suspected of causing genetic defects
- H350 May cause cancer
- H351 Suspected of causing cancer
- H360 May damage fertility or the unborn child
- H361 Suspected of damaging fertility of the unborn child †Score based upon a 100% active material.

FIG.13

CEPR RESULTS FOR CHEMICALS COMMONLY USED IN ENERGY INDUSTRY APPLICATIONS

| Chemical | CAS # | HDS* | OSPAR Pre-Screen Estimate | H- Phrases** | Total Regulatory Count | Estimated CEPR SCORE† | Comments |
|---|---|---|---|---|---|---|---|
| Acetic acid (≤10% aqueous solution)‡ | 64-17-7 | No | Pass | None | 1 | 0 | Acidizer |
| Choline chloride | 67-48-1 | No | Pass | None | 0 | 0 | KCl Substitute |
| Citric acid | 77-92-9 | No | Pass | None | 0 | 6 | Chelating agent |
| Ethylene glycol | 107-21-1 | No | Pass | None | 4 | 0 | Solvent |
| Glutaraldehyde (25% aqueous solution) | 111-30-8 | No | Pass | None | 1 | 6 | Biocide |
| Glutaraldehyde (100% active)⁹ | 111-30-8 | No | Pass | None | 1 | 21 | Biocide |

*Highly Discouraged Substance (HDS)
**The following H phrases were considered:
- H340 May cause genetic defects
- H341 Suspected of causing genetic defects
- H350 May cause cancer
- H351 Suspected of causing cancer
- H360 May damage fertility or the unborn child
- H361 Suspected of damaging fertility of the unborn child †Score based upon a 100% active material or, where noted, at field supplied concentrations.
‡Field supplied acetic acid is usually 10% or less active in water.
⁹Field supplied glutaraldehyde is usually 25% active in water.

FIG. 14

Relative hazard ranking of ten chemistries using the CEPR process; numeric hazard score and regulatory "hits".

METHODS, SYSTEMS AND COMPUTER PROGRAM PRODUCTS FOR CHEMICAL HAZARD EVALUATION

CROSS REFERENCE TO RELATED APPLICATIONS

This application claims the benefit of an earlier filing date from U.S. Non-Provisional application Ser. No. 14/048,188 filed Oct. 8, 2013, the entire disclosure of which is incorporated herein by reference.

BACKGROUND OF THE INVENTION

Chemical hazard assessment is an important aspect in the evaluation of existing chemical products, and in the development of new chemical products. For example, in the energy industry, various chemical components and substances are incorporated in products used for various energy industry activities, such as oilfield drilling, evaluation, completion, stimulation and production activities A wide variety of chemical raw materials, intermediates and products used in energy industry applications may have environmental and safety impacts that affect their use. Such chemicals should be evaluated to ascertain potential environmental and health effects.

BRIEF SUMMARY OF THE INVENTION

A method of assessing chemical products includes: receiving input data including identification of a chemical substance at a processing device; evaluating a regulatory impact of the chemical substance based on at least one of global regulation data, regional regulation data and jurisdiction-specific regulation data, and outputting a regulatory impact assessment; evaluating potential hazards posed by the chemical substance based on available data related to characteristics of the chemical substance by comparing the characteristics to a plurality of criteria including environmental criteria, toxicity criteria related to effects on human health, and physical criteria related to hazards encountered during material transportation and handling, and outputting a chemical hazard assessment; and generating a chemical assessment report indicating potential impact due to use of the chemical substance, the chemical assessment report indicating chemical assessment results that include the regulatory impact assessment and the chemical hazard assessment.

A system for assessing chemical products includes: a data storage and retrieval device configured to at least one of receive and store source data, the source data including available data related to characteristics of chemical substances and regulatory data including at least one of global regulation data, regional regulation data and jurisdiction-specific regulation data; and a processing device communicatively coupled to the data storage and retrieving device, the processing unit including an input component configured to receive input data including identification of a chemical substance. The processing device is configured to perform: evaluating a regulatory impact of the chemical substance based on the regulatory data, and outputting a regulatory impact assessment; evaluating potential hazards posed by the chemical substance based on the available data by comparing the characteristics to a plurality of criteria including environmental criteria, toxicity criteria related to effects on human health, and physical criteria related to hazards encountered during material transportation and handling, and outputting a chemical hazard assessment; and generating a chemical assessment report indicating potential impact due to use of the chemical substance, the chemical assessment report indicating chemical assessment results that include the regulatory impact assessment and the chemical hazard assessment.

BRIEF DESCRIPTION OF THE DRAWINGS

The following descriptions should not be considered limiting in any way. With reference to the accompanying drawings, like elements are numbered alike:

FIG. 4 depicts a portion of an exemplary computer program for receiving input data, performing the method and generating a chemical assessment result;

FIGS. 5, 5-1 and 5-2 collectively referred to as FIG. 5, depict a regulatory impact assessment portion of a computer program for performing the method of FIG. 3;

FIG. 6 depicts a decision tree illustrating an exemplary process of performing the regulatory impact assessment;

FIGS. 7 and 7-1, collectively referred to as FIG. 7, depict a pre-screen prediction portion of a computer program for performing the method of FIG. 3;

FIGS. 8 and 8-1, collectively referred to as FIG. 8, depict a chemical hazard evaluation portion of a computer program for performing the method of FIG. 3;

FIG. 9 displays exemplary environmental criteria used in performing the chemical hazard evaluation of FIG. 8;

FIGS. 10A and 10A-1, and FIGS. 10B, 10B-1 and 10B-2, collectively referred to as FIG. 10, display exemplary toxicity criteria used in performing the chemical hazard evaluation of FIG. 8;

FIG. 11 displays exemplary physical hazard criteria used in performing the chemical hazard evaluation of FIG. 8;

FIG. 13 illustrates an exemplary chemical assessment result;

FIG. 14 illustrates an exemplary chemical assessment result; and

DETAILED DESCRIPTION

Figure 1:
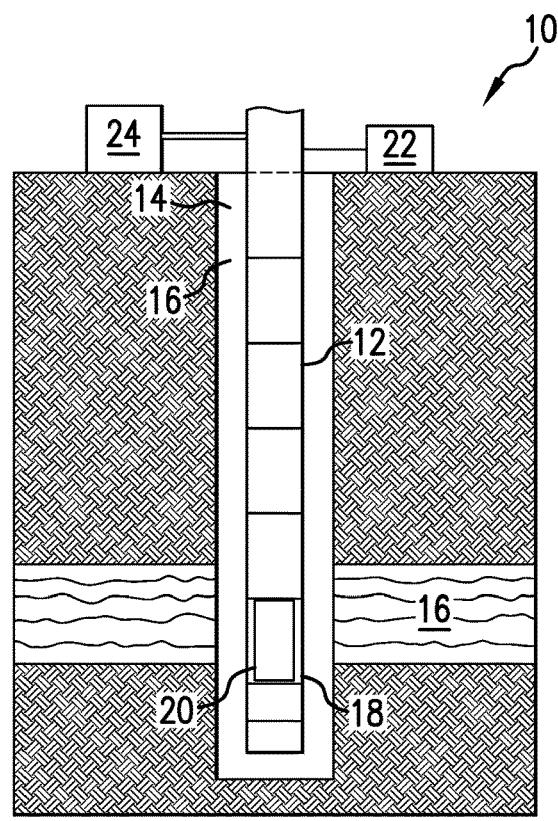
FIG. 1 depicts an embodiment of a well logging, production and/or drilling system.

Systems and methods are provided for evaluating chemical substances such as compounds, components and/or products, and generating chemical evaluation summaries, reports, scores or other outputs. Exemplary chemical substances include chemicals, constituents and products used in the oil and gas industry, such as components of fluids used for drilling, evaluation, completion, stimulation (e.g., hydraulic fracturing), production, transmission and refining of hydrocarbons (e.g., oil and natural gas). As described herein, a "chemical substance" collectively refers to any combination of one or more substances, components and products. Substances include, e.g., chemical constituents such as chemical elements and/or compounds and combinations thereof, components of chemical products include fluids or substances used to manufacture a product, and products include any manufactured material than can be used in energy industry applications.

The systems and methods provide an integrated tool for assessing the intrinsic properties of new and existing chemical substances and products and the potential impact such products will have on human health and the environment. The systems and methods also provide an excellent understanding of, and means to communicate, the existing or potential level of worldwide regulatory burden a product may present.

An embodiment of a processing device is configured to execute an algorithm or workflow that receives data for one or more chemical substances from various sources, and generates an assessment of a chemical substance based on criteria including environmental impact criteria, a regulatory impact assessment and chemical hazard criteria. The processing device is configured to generate an assessment output or result such as a chemical assessment report that provides information regarding potential impacts, including environmental and regulatory impacts. In one embodiment, one or more scores or other numerical values are provided to communicate relative levels of various potential impacts associated with use of the chemical substance or substances.

Embodiments of methods include evaluating a chemical substance against various evaluation criteria and providing a chemical assessment result (e.g., a report and/or score) that indicates potential impacts due to use of the chemical substance. An embodiment of a method is a Chemical Evaluation Process Review (CEPR) which includes evaluating a chemical substance against criteria, including environmental impact, toxicological impact, physical impact and regulatory impact. The chemical substance is evaluated using these criteria to generate a chemical assessment result including at least a hazard summary and/or score, and a regulatory impact summary and/or score. For example, a report or other result includes a hazard summary that includes a score or other quantitative result, and a regulatory impact summary that includes a qualitative result (e.g., identification of applicable regulations and their effect on the use of the chemical substance) and may also include a quantitative result (e.g., regulatory score based on the number of identified regulations).

In one embodiment, the device and method are configured to output a chemical substance assessment result. Results from one or more individual chemical substance assessments can be stored in a database or other storage. Previously generated results from individual chemical substance assessments may be combined to generate accumulated results for chemical products comprising multiple substances.

FIG. 1 illustrates an exemplary embodiment of a well logging, exploration, production and/or drilling system 10 for which chemical substances or products may be employed. The system 10 includes a toolstring or borehole string 12 that is shown disposed in a borehole 14 that penetrates at least one earth formation 16 during a drilling, well logging and/or hydrocarbon production operation. In one embodiment, the system 10 includes a bottomhole assembly (BHA) 18. The BHA 18, or other portion of the borehole string 12, includes a tool 20 configured to perform one of various functions. A control device 22 (e.g., a surface control and/or processing unit) is coupled to the string 12, and a fluid storage device 24 (e.g., tank or mud pit) is configured to provide a borehole fluid to the string 12 and/or borehole. For example, the tool 20 includes a drilling assembly and a drilling fluid such as drilling mud is circulated in the borehole during drilling. For stimulation operations the borehole fluid includes fracturing fluid that is forced downhole to stimulate production of hydrocarbons. Other types of fluids could be various gases or liquids for facilitating hydrocarbon production, and water management. Such fluids include various chemical constituents that may be evaluated using the methods described herein.

Figure 2:
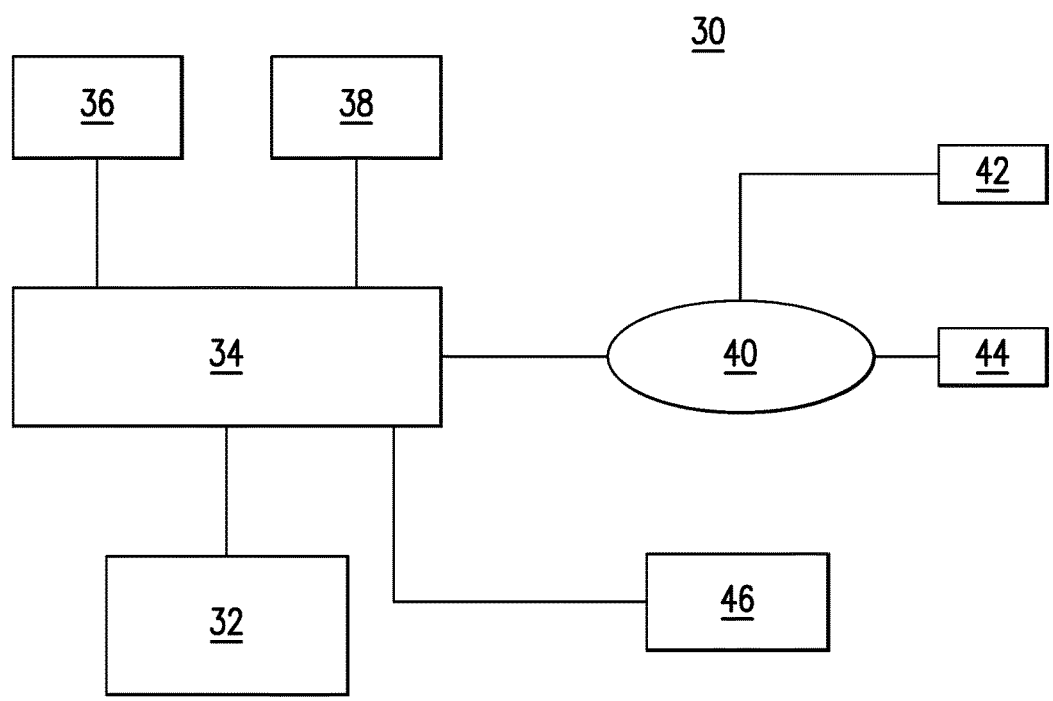
FIG. 2 depicts an embodiment of a data processing and chemical assessment system.

Referring to FIG. 2, an embodiment of a data processing and chemical assessment system 30 is shown. The system 30 includes a processing device or unit 32 such as a computer (e.g., desktop or laptop), which may be connected to a host 34. The processing unit 32 and the host 34 are not limited to the configurations described herein, and may include any suitable device or network including various processors, memory and communications devices.

In one embodiment, the host 34 includes a processor, memory, input/output devices and other components for execution of a computer program or algorithm to perform the methods described herein. The host 34 is connected to various data storage locations, which may be internal or external to the host 34. For example, the host 34 is connected to databases which store lists, libraries or other data structures that store information used to assess chemical substances as described herein. Exemplary databases include a "Highly Discouraged Substances" list database 36 and a regulatory database 38. The host 34 may also be connected to a network such as the Internet 40 to allow the host 34 to retrieve information from various sources, such as regulatory sources 42 and chemical industry or scientific sources 44. In one embodiment, the system 30 includes a storage location or device, such as a chemical assessment database 46, to store results of individual chemical substance and multiple substance product assessments.

The methods described herein can be performed or executed on the client computer, the host or any other processing unit or combination of processing units. In one embodiment, the method is performed exclusively by a processor using, e.g., input data identifying one or more chemical substances, constituents or products. In other embodiments, the method is performed in conjunction with a user. For example, the processor may provide a platform for data input, provide access to chemical substance data, and calculate regulatory and/or hazard scores. A user may provide other components of the method, such as data selection, assessment descriptions or summaries and evaluation of data quality.

The system 30 is configured to perform a chemical assessment or evaluation method (e.g., Chemical Evaluation Process Review (CEPR)). The method uses global data sources to evaluate chemical substances and products through a practical, transparent and quantitative process, based upon their potential physical, health and environmental impacts. The process also includes a review of global regulatory requirements (e.g., chemical prescreening, transportation, handling and application) and provides an assessment of the potential regulatory impact of a chemical substance or product. The method can be performed for a chemical substance or combinations of substances, a chemical constituent, a chemical product (e.g., including multiple substances or constituents) or a fluid system composed of multiple products (collectively referred to herein as a "chemical substance").

In one embodiment, the method provides a relative numerical hazard ranking score for chemical substances, and also provides a qualitative regulatory impact assessment including, e.g., a regulatory impact result such as a numerical indicator based on a number of applicable regulations and/or a list of applicable regulations. For example, the process identifies global and geomarket-specific regulatory obligations associated with usage of a chemical substance. In addition, the method may include a pre-screen prediction process for the chemical substance, by which characteristics of the chemical substance are compared to a pre-existing chemical evaluation standard. For example, the pre-screen process estimates the likelihood that a product or component, including the chemical substance, can be used in areas or countries which have adopted all or portions of the Oslo-Paris Convention (OSPAR) Harmonized Mandatory Pre-screening Scheme criteria.

One embodiment of a chemical assessment method includes one or more of four assessment elements: Highly Discouraged Substances, Regulatory Impact Assessment, Pre-Screen Prediction, and Chemical Hazard Evaluation. As described in embodiments herein, all four of these assessment elements are utilized in providing an overall chemical assessment. However, in some embodiments, the method includes one or more of the assessment elements.

The "Highly Discouraged Substances" assessment elements compares the chemical substance to widely known and well-studied substances which have been determined, by the international scientific community, to persist in the environment, bioaccumulate through the food chain, and pose a risk of causing serious adverse effects to human health and the environment. As a result, the assessment may highly discourage the intentional addition of any of these substances into chemical products.

The "Regulatory Impact Assessment" element provides an understanding of potentially applicable regulations and their impact for chemical substances and/or products being developed or used. As described herein "regulatory impact" refers to any effects on, or restrictions to, the use of chemical substances or products due to regulations imposed by governmental authorities or other entities having regulatory authority. Not intended to replace or supersede laws and regulations that are in force, this assessment is especially useful during research and development to understand potential regulatory implications before releasing a chemical product to market. This assessment identifies global, regional and/or country-specific or jurisdiction-specific regulations that may apply to the chemical substance and would thus have a regulatory impact, i.e., an impact on the use of such a substance in corresponding jurisdictions.

The regulatory impact assessment may be used to create regulatory assessment results including text, lists, tables or other data structures that identifies potential regulatory challenges. The data structure may include identification of regulatory bodies, and/or the number and/or list of applicable regulations associated with the regulatory impact. The actual number and type of regulations are not limited to the embodiments described herein Exemplary sources that can be used in determining the potential level of globally or regionally applicable regulatory control and impact include Material Safety Data Sheets/ Safety Data Sheets (MSDS/SDS), and reports in other regulations for chemical products. The presence of certain substances in a product may trigger specific regulatory obligations such as reporting or record keeping. Regulatory impacts could range from Community Right-To-Know notifications through MSDS/SDS statements to actual restrictions or bans on product use within a given jurisdiction.

In one embodiment, searches of global, national, regional and state regulatory lists performed during this assessment generate qualitative information that can be used to develop or modify products with fewer hazards, while also reducing the regulatory obligations associated with more hazardous products. In this way, developing and offering products with fewer hazards can reduce or minimize potential marketing barriers and concerns from a variety of stakeholders. This can be an especially powerful tool to demonstrate the success of continuous product improvement. For example, as MSDS/SDSs are an effective means to communicate hazard information to a wide audience, the fact that fewer and fewer hazards must be identified in successive MSDS/SDSs for a given product is proof of advancements in the chemical product formulation and development process. In this way, developing and offering products with fewer hazards can communicate to a wide variety of stakeholders the industry's commitment to developing less hazardous products.

The "Pre-screen Prediction" is also a useful element of the chemical assessment method. The pre-screen prediction element evaluates the chemical substance against selected pre-screen criteria from pre-existing standards. For example, the Oslo-Paris Convention (OSPAR) is the mechanism by which the European Community and 15 governments of the western coasts and catchments of Europe protect the marine environment of the North Sea. The OSPAR Harmonised Mandatory Control Scheme (HMCS) comprises a Harmonised Pre-screening scheme (OSPAR Pre-screen). The regulatory purpose of the OSPAR Pre-screen is to allow authorities in the North Sea to identify and regulate hazardous and non-hazardous substances in offshore chemicals, and to substitute and phase out those substances identified as hazardous. Although the Pre-screen was originally designed and intended for offshore chemical usage in the North Sea, several other countries and jurisdictions have adopted (in whole or in part) the Pre-screen scheme as a means to evaluate and regulate chemicals for both onshore and offshore use. As a result, chemical product usage in a number of markets is becoming increasingly dependent on whether a chemical substance or product will meet criteria set forth in the OSPAR Pre-screen scheme.

The pre-screen prediction element is used to evaluate available data against selected criteria from a pre-screen scheme or standard. For example, the pre-screen prediction evaluates eco-toxicity data against selected OSPAR Pre-Screen scheme criteria and provide a preliminary assessment of the likelihood that a chemical substance and/or product would be accepted for use or would require substitution. The pre-screen element may also compare the chemical substance to a list of substances, maintained by OSPAR, which are considered to pose little to no risk to the environment (PLONOR) and are automatically eligible for use.

A formal submittal of eco-toxicity data to OSPAR, in the form of a Harmonised Offshore Chemical Notification Format (HOCNF) document, for the purpose of regulatory review and approval requires studies be conducted using a specific set of test protocols with data requirements which require the use of certain marine organisms, and refer to three key endpoints: aerobic biodegradation, bioaccumulation and aquatic toxicity. A tremendous body of environmental toxicity data has been collected from alternate freshwater and marine species which may also have been conducted using studies that follow alternate but standardized protocols such as Environment Canada, United States Environmental Protection Agency (USEPA), and Organization of Economic Cooperation and Development (OECD).

This element of the chemical assessment method compares the chemical substance and/or product to Pre-Screen Prediction criteria (examples of which are shown in FIG. 6) to determine whether the product has been assessed and, if so, whether it has "passed" or "failed". If data for the chemical substance or product, such as those required for a formal HOCNF submittal, are not available, the assessment enables a user to evaluate alternate, reliable, relevant, and adequate data for the substance or product against the Pre-Screen Prediction criteria and provide a qualitative, preliminary prediction of whether the chemical product might pass or fail.

The "Chemical Hazard Evaluation" element identifies one or more categories of hazards that are quantitatively assessed. For example, this evaluation includes assessment of the chemical substance and/or product in environmental, toxicological and physical hazard categories. Although embodiments described herein utilize all three of these categories, fewer categories may be used, or other combinations of these categories and/or other categories could be employed.

A numerical result or score may be provided as an output of the chemical hazard evaluation element. The score may be based on various hazard characteristics. In one embodiment, the score is an accumulated or combined score based on a plurality of chemical substances or constituents. For example, a combined score is generated for a chemical product including a plurality of substances (i.e., constituents), and/or for a material or fluid system that includes multiple substances and/or products (i.e., constituents). The combined score may be generated by weighting the score for each constituent or product based on its proportion of the product and/or system. For example, the fluid system or product is assigned a score based on the score for each constituent that is weighted based on its percentage (e.g., by mass, weight or volume) within the system. This allows for calculating a total hazardous impact for a fluid product or system and comparisons of systems, or a total hazardous impact for a wellsite, lift of well, location or facility.

The chemical hazard assessment element, in one embodiment, includes one or more hazard categories and/or criteria that are taken from pre-existing evaluation standards. For example, the chemical hazard element incorporates categories and/or criteria for evaluating chemical hazards from, or includes categories and/or criteria based on or patterned after, the United Nations' Globally Harmonized System of Classification and Labeling (GHS), the USEPA Design for the Environment (DfE), and others. The chemical hazard element may use categories and/or criteria based on any number of standards, e.g., using criteria from the GHS standard and any number of other standards. In one embodiment, suitable categories and/or criteria are selected from such standards that would have applicability to the energy industry.

Figure 3:
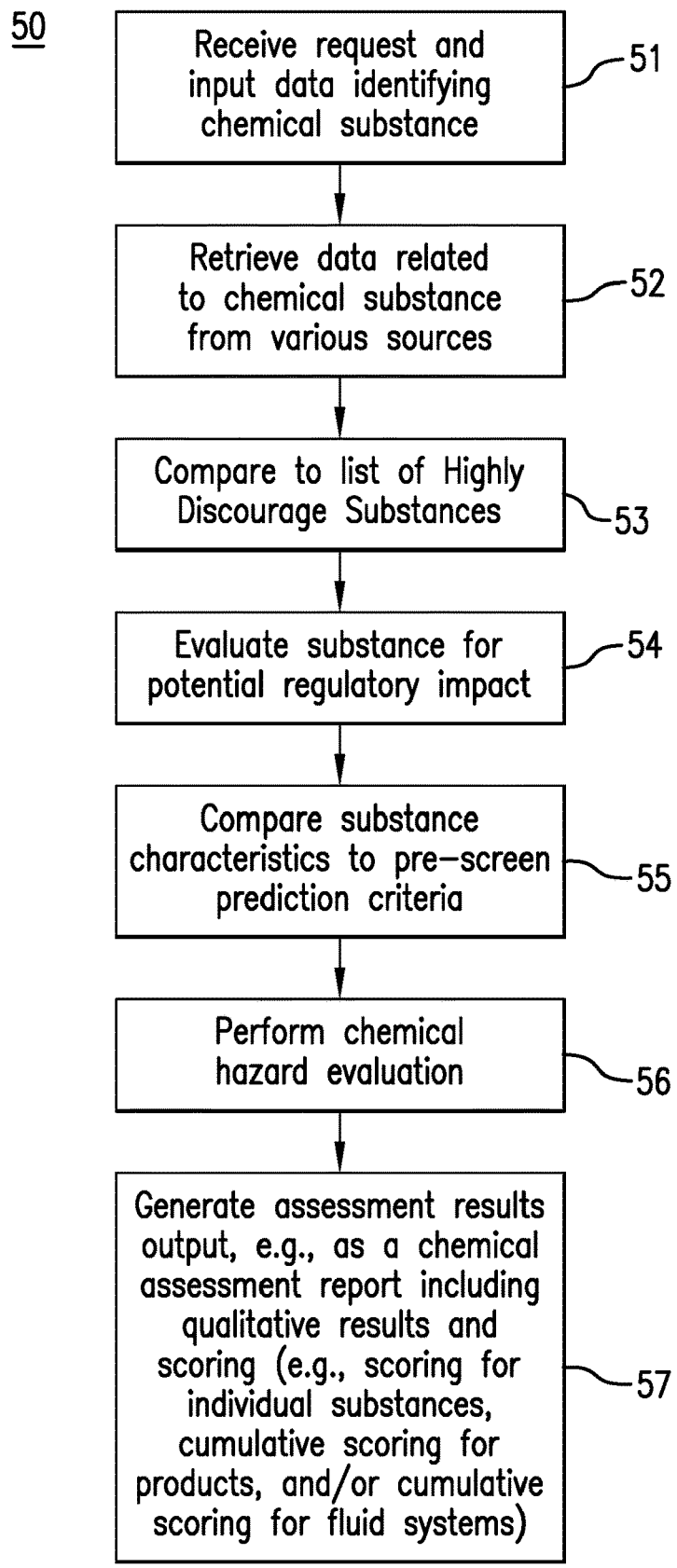
FIG. 3 is a flow chart illustrating an embodiment of a method of assessing the potential impact of one or more chemical substances or products.

FIG. 3 is a flowchart depicting an exemplary method 50 of assessing a chemical product, compound, substance, constituent or component, collectively referred to herein as a "chemical substance." The method 50 may be performed on any suitable processor, processing device and/or network, such as the processing system 30 or components thereof. The method 50 includes one or more stages 51-57. In one embodiment, the method 50 includes the execution of all of stages 51-57 in the order described. However, certain stages may be omitted, stages may be added, or the order of the stages changed.

An example of a chemical assessment program is shown in FIGS. 4-11, which provides a means to store assessment data (e.g., substance information such as Highly Discourage substance list, and regulatory information) and instructions for assessment, as well as locations of data used for assessment. In this example, the program provides a workbook including a number of spreadsheets that are used to input information, generate assessment results and provide assessment outputs such as reports or summaries. The workbook in this example includes specific tabs for each component of the evaluation process, and scoring guidelines for each hazard endpoint. The spreadsheet may be controlled and managed by any suitable processing device. Assessment results for specific chemical substances or combinations may be stored as workbook and/or document files for later analysis and/or retrieval.

In one embodiment, for assessment of chemical products that have multiple constituents, a product level workbook may be compiled based on assessments of the individual constituents. For example, a product level workbook includes scores and data compiled for each substance in a product. An appropriate storage (database or library) stores both constituent workbooks and product level workbooks.

In the first stage 51, a processing device receives a request for assessment of a chemical substance. The processing device determines if the substance has previously been assessed and an assessment result has been generated. For example, the client processor searches or requests data from the chemical assessment database 46. If an assessment result exists, the assessment result may be output to a user or other location, and/or used to generate an accumulated assessment output if the chemical substance is a constituent of product. If the assessment result does not exist, the method 50 proceeds to stage 52 and performs the chemical assessment.

In the second stage 52, data related to the chemical substance is retrieved. Such data includes information regarding intrinsic hazard characteristics of the chemical substance, and is taken from various sources, such as regulatory sources and industry or scientific sources. Exemplary sources include regulatory bodies that maintain information regarding different substances, collections of reports such as MSDS/SDS databases, and collections of studies relating to the chemical substance (e.g., internal studies, studies performed by product manufacturers and studies performed by scientific bodies). Other useful sources of information should provide data that are reliable, relevant, and adequate for the hazard category being assessed.

In the third stage 53, the chemical substance is compared to a list or other data structure that identifies a number of substances that should be avoided if possible, and are highly discouraged from being intentionally added or formulated into any chemical product, at any concentration. Such substances are referred to as "Highly Discouraged Substances."

The list may include any number of substances that are known to pose significant risks to the environment or human health. In one embodiment, the list includes substances which pose known, generally internationally agreed-to, significantly adverse effects to human health, and the environment. The list may be taken from a pre-existing source, such as a regulatory or scientific source. The list may also be constructed from combinations of sources and is subject to modification as new data becomes available.

For example, several well-characterized and prevalent pollutants, such as PCBs, dioxins, benzo[a]pyrene, halogenated aromatic hydrocarbons and others have Persistent, Bioaccumulative, and Toxic (PBT) characteristics which pose a significant risk of adverse effects to human health and the environment. Challenges in controlling these Persistent Organic Pollutants (POPs) result from their ability to transfer rather easily between air, water, and land, and to travel long distances. Several studies have shown that many of these substances have bioaccumulated throughout the global food chain, leading to body burdens far in excess of levels found in the environment. With frequent exposure over time, the amount present in an organism's tissues can build up and cause toxic effects. In humans, demonstrated adverse effects include nervous system abnormalities, reproductive and developmental problems, cancer, and genetic impacts. Young children and developing fetuses may be at especially high risk.

Exemplary Highly Discouraged substances are listed in the spreadsheet of FIG. 4. As shown, the Highly Discouraged list includes substances identified by the United Nations Environment Programme and the United States Environmental Protection Agency (USEPA).

If the chemical substance is found in the Highly Discouraged Substances list, the appropriate output generated by the method indicates as such and may also provide guidelines for use, substitution, and/or exclusion of the substance in the chemical product.

In the fourth stage 54, the chemical substance is evaluated for potential regulatory impact, i.e., a regulatory impact assessment is performed. The regulatory impact assessment component provides an understanding of potentially applicable regulations and their impact for constituents and products being developed or used. Applicable regulations and/or regulatory bodies are identified, and their respective effects and restrictions on the chemical products are assessed to determine the regulatory impact that would effect.

The regulatory impact could range from the requirement to notify through MSDS/SDS statements to actual restrictions or bans on use. This assessment is designed to provide a view of hazardous material regulations that may apply to a substance or product. Regulations included in this section may be global, regional, and/or country- or jurisdiction-specific in scope. Thus, the regulatory impact may be based on at least one of global regulations, regional regulations and jurisdiction-specific regulations. Being present on a substance list or lists maintained by a regulatory body indicates potential regulatory obligations that may need to be met before a product can be developed for commercialization in a corresponding market.

Various sources of regulations, such as databases or libraries of regulations and/or regulatory bodies, are consulted to determine whether the chemical substance would be subject to any regulations and may also be analyzed to determine what the potential impact of applicable regulations would be. The "impact" is considered to include the type and extent of restrictions on use of the chemical substance in various applications, such as energy industry applications. The impact may also include the geographic impact or restrictions on types of environments or population areas. Accordingly, this stage may include generating an output that provides qualitative information regarding regulatory impact (e.g., identifying applicable regulations and their restrictions on use). In addition, the number and/or list of applicable regulations may be generated based on the assessed impact.

For example, the output generated by this assessment may include a description of the impact of applicable regulations, such as restrictions on transportation, required MSDS warnings, targeting for replacement, risk management procedure, monitoring, and reporting. In addition to the description of existing regulations, the output may indicate whether future regulations are contemplated, and may also offer information regarding potential chemical substances as substitutions.

In one embodiment, the number and/or list of applicable regulations is included in the output, based on the number of regulatory lists that a substance is present on.

FIG. 5 illustrates a spreadsheet utilized in the Regulatory Impact Assessment element, which includes a list of regulations and/or regulatory authorities. Each of these regulations are consulted (e.g., a regulatory database is searched for the chemical product) to determine which, if any, of the regulations apply to the substance, product or component. The presence or absence of the substance on each list is notated in the spreadsheet. In addition, the total number of applicable regulatory lists, for each substance, is tabulated and may be included in the output. Such lists may include global regulations, regional regulations and/or country- or jurisdictional regulations. The list of regulations evaluated in this example include:

Globally Applicable Regulatory Lists

International Agency for Research on Cancer (IARC)—Carcinogens: The IARC is part of the World Health Organization, and conducts research on mechanisms of carcinogenesis and identifies known or suspected human carcinogens. In general recognized carcinogens are targets for replacement by consumers and may have regulatory obligations associated with their use.

UN Environment Programme (UNEP) Banned Chemicals: The UN General Assembly Resolution 37/137 from 1982 initiated the List of Products whose Consumption and/or Sale have been Banned, Withdrawn, Severely Restricted, or Not Approved by Governments. This list is published by the UNEP and describes regulatory actions taken.

Eastern Hemisphere (Regional and Country/Jurisdiction Specific) Regulatory Lists EUROPA Annex 13 Category 1 Endocrine Disruptors: The European Commission DG ENV commissioned conducted a study on endocrine disruption, with a focus on man-made chemicals. The resulting report, "Towards the establishment of a priority list of substances for further evaluation of their role in endocrine disruption—preparation of a candidate list of substances as a basis for priority setting," published in November 2000, summarized the results of the study, and provided a list of 146 substances listed with endocrine disruption classifications.

European Chemicals Agency Substances of Very High Concern: The European Chemicals Agency (ECHA) list of substances of very high concern includes substances which are: Carcinogenic, Mutagenic or toxic to Reproduction (CMR) classified in category 1 or 2, Persistent, Bioaccumulative and Toxic (PBT) or very Persistent and very Bioaccumulative (vPvB) according to the criteria in Annex XIII of the EUs Registration, Evaluation, Authorization and Restrictions of Chemicals (REACH) Regulation, and/or identified, on a case-by-case basis, from scientific evidence as causing probable serious effects to humans or the environment of an equivalent level of concern as those above e.g. endocrine disrupters.

European Commission Priority Substances & Certain Other Pollutants: This commission was created in accordance with Annex II of the Directive 2008/105/EC. The list includes comprises 41 substances or substance groups (33 priority substances and 8 certain other pollutants. Priority substances or substance groups include polyaromatic hydrocarbons (PAH), biocides, and metals. Certain other pollutants are not included in the priority substances list, and fall under the scope of Directive 86/280/EEC.

OSPAR Chemicals for Priority Action: The List of Chemicals for Priority Action contains 42 substances or groups of substances that have been prioritized by OSPAR for monitoring and control of emissions to the marine environment. It is noted that assessment of regulatory impact using this list may be performed as part of an assessment element that is separate from the OSPAR Pre-screen assessment element discussed in further detail below.

Australia Air Toxics Program—Priority Pollutants: The Australian Department of Sustainability, Environment, Water, Population, and Communities established a list of priority air toxics via the Report of the Technical Advisory Group on Prioritisation of Air Toxics for Living Cities Air Toxics Program. The list includes a variety of substance types, including metals, volatile organic compounds, and PAHs, that have characteristics that may be a hazard to human, plant or animal life.

Australian Drinking Water Guidelines: The Australian Government National Health and Medical Research Council published the 2004 Australian Drinking Water Guidelines to supply guidelines on safe drinking water. The list of potential hazardous agents in drinking water comprises Part V of the Guidelines, and identifies microbial, chemical, physical, and radiological agents.

Australia National Pollutant Inventory Guide to Reporting: The National Pollutant Inventory (NPI) is a database describing air, land, and water emissions of 93 substances from industrial facility and diffuse sources. The purpose of the NPI is to provide operators with a means of estimating emissions and to determine whether emissions of NPI substances should be reported.

ERMA New Zealand Reassessment Priority List: The New Zealand Environmental Risk Management Authority (ERMA) publishes the reassessment priority list. Listed substances are approved for use in New Zealand, but are identified for reassessment because ERMA will consider the adequacy of safety precautions and whether listed substances should remain approved for use.

Western Hemisphere (Regional and Country/Jurisdiction Specific) Regulatory Lists U.S. Department of Transportation (USDOT) Marine Pollutant: As required by 49 CFR, Parts 100-180, the USDOT regulates the packaging, labeling, and transport of marine pollutants.

National Toxicology Program (NTP)—Carcinogens: The NTP, under the U.S. Department of Health and Human Services, evaluates chemical agents of public health concern. The NTP Report on Carcinogens identifies agents, substances, mixtures, and exposure circumstances that are determined to be known or reasonably anticipated to cause cancer in humans by the NTP.

EPA Safe Drinking Water Act Maximum Contaminant Levels: The Safe Drinking Water Act (Title 40, Ch. 1, Part 141) authorizes the USEPA to establish national health-based standards for drinking water. The EPA enforces National Primary Drinking Water Regulations (NPDWR), standards that apply to contaminant levels in public water systems to limit the level of contaminants present in drinking water. Each contaminant is associated with a Maximum Contaminant Level, the highest level of a contaminant that is allowed in drinking water. The presence of these substances above threshold criteria will result in a range of regulatory requirements. The levels of these substances in certain energy industry products may be a concern, prompting substitution where possible.

EPA Clean Water Act Priority Pollutants: Priority Pollutants, listed in Appendix A, 40 CFR Part 423, are a set of substances regulated by the EPA and for which the EPA has published analytical test methods. Regulatory requirements and restrictions may be imposed in certain jurisdictions related to a chemical products use in the energy industry.

EPA Hazardous Air Pollutants: Clean Air Act Amendments published in 1990 directed the EPA to establish standards for major sources of air toxics and identified the List of Hazardous Air Pollutants (HAPS). A range of requirements including emission controls may be imposed on facilities emitting these substances.

Hazardous Volatile Organic Chemicals: The USEPA and US Geological Society (USGS) have identified up to 104 VOCs which have the potential to adversely impact human health and the environment. These chemicals have been identified based upon physical properties, cancer and non-cancer hazard potential, toxicity to aquatic organisms, occurrence in indoor air, groundwater, surface water and drinking water sources, potential for atmospheric ozone depletion, and bioconcentration by aquatic organisms. Specifically these are referenced in the 2006 EPA Building Assessment Survey and Evaluation Study, and the 1999 USGS Open File Report 99-182.

EPCRA Sec. 302 Extremely Hazardous Substances: Section 302 of the Emergency Planning and Community Right to Know Act (EPCRA) establishes a list of Extremely Hazardous Substances (EHS) for which facilities must report storage, use, and release. In general, all facilities using substances on the Section 302 list at concentrations above established thresholds may have reporting requirements and additional requirements may apply.

EPCRA Sec. 313 Toxic Chemicals: Environmental release data, including waste management and emissions, for chemicals and chemical categories listed under Section 313 of the EPCRA must be reported annually.

US DOT Environmentally Hazardous Chemicals: The US DOT Hazardous Materials Table (HMT) contains over 3600 substances and substance categories which are associated with packaging regulations and shipping quantity limitations.

US FDA Generally Regarded As Safe (GRAS) List: GRAS is an FDA designation that a chemical or substance, specifically when added to food, is considered safe by experts. This designation is granted for substances generally recognized, through a consensus of opinion by FDA and other experts, as having been adequately shown through scientific procedures or common experience in use, to be safe under the conditions of their intended use (as a food additive).

Environment Canada—Acts & Regulations—Toxic Substances List—Schedule 1: The Canadian Environmental Protection Act (CEPA 1999, Part 5) authorizes the Minister of Health and Minister of the Environment to manage toxic substances and to establish substance lists. Substances reported on the List of Toxic Substances were determined to be toxic based on risks that the substance poses to the environment or human health as described in section 64 of CEPA.

Environment Canada—Acts & Regulations—Priority Substance List: The CEPA 1999, section 76, requires that the Minister of the Environment and the Minister of Health establish a Priority Substances List (PSL) identifying substances to be assessed to determine potential health or environmental risks.

Another exemplary source of regulatory impact information is the GHS standard and Annex VI of Regulation (EC) No 1272/2008 (CLP Regulation). For example, portions of these standards may be used to evaluate hazards of the chemical substance. Example substances classified by the GHS scheme include those identified as including carcinogens, mutagens and reproductive toxins (CMRs). The following table is a summary of harmonized (classified) hazard phrases or "H" phrases used in the GHS standard to identify types of hazards associated with CMR substances:

| GHS/CLP HAZARD PHRASES ASSOCIATED WITH CARCINOGEN, MUTAGEN, and REPRODUCTIVE TOXINS | |
| --- | --- |
| H340 | May cause genetic defects |
| H341 | Suspected of causing Genetic Defects |
| H350 | May cause cancer |
| H351 | Suspected of causing cancer |
| H360 | May damage fertility or the unborn child |
| H360 | Suspected of damaging fertility or the unborn child |

Each hazard phrase for all CMRs is clearly noted so that implications for a specific level of hazard associated with a product can be accurately considered.

Although the majority of lists are provided to identify potential regulatory challenges, one or more of these lists may offer positive attributes. For example, the GRAS list, described above, includes substances that are generally recognized to be safe under the conditions of their intended use (as a food additive). It is noted that, even though chemical products such as oilfield products include substances found on the GRAS list, this does not imply that the chemical substances used in the manufacture of the chemical products are "food grade." Essentially, this information can be used to convey the low level of hazard posed by these substances.

In the fifth stage 55, the chemical product is assessed based on pre-screen criteria provided by a pre-existing chemical evaluation standard, such as the OSPAR Pre-screen scheme criteria. This assessment element evaluates available toxicity, biodegradation, and bioaccumulation data against Pre-screen Prediction criteria and provides a preliminary assessment of the likelihood that products/substances would be accepted for use or would require substitution. (Exemplary criteria are shown in FIG. 6) If the chemical substance or product has already been formally evaluated by OSPAR, the results of such an evaluation are acquired and presented as part of the assessment output.

This element of the assessment method acquires (or attempts to acquire) data for the chemical product to be used in the OSPAR Pre-Screen Prediction. In one embodiment, the element assesses the product under all the Pre-Screen Prediction criteria. In one embodiment, the element does not assess the product under all of the Pre-Screen Prediction criteria, but may select a number of tests or requirements to determine whether the product would likely meet Pre-Screen criteria.

In one embodiment, data from all or some of the following tests and protocols are assessed to determine whether the product would likely meet Pre-Screen criteria. Such tests and protocols include:

1. Aquatic Toxicity (with Acceptable Species and Test End-Point)
    ISO/DIS 10253—Water quality—Marine algae growth inhibition test (*Skeletonema costatum, Phaeodactylum tricornutum*, 72 hr. EC50)
    ISO TC 147/SC5/WG2—Toxicity to Invertebrates (*Acartia tonsa, Mysidopsis bahia*, 48 hr. LC50)
    PARCOM Protocol 1995 Part B—Fish Acute Toxicity Test (*Scophthalmus maximus, Cyprinodon variegatus*, 96 hr. LC50)
    PARCOM Protocol 1995 Part A—Sediment Reworker Toxicity Test (Corophium volutator, Corophium sp., 10 day LC50).

2. Biodegradation
    OECD 306—Biodegradability in Seawater Marine Bodis test
    OECD 301C—Ready Biodegradability: MITI test
    OECD 301D—Ready Biodegradability: Closed bottle test
    OECD 301E—Modified OECD Screening test
    OECD 301F—Manometric Respirometry
    OECD 310—Ready Biodegradability: Headspace test
    Freshwater Bodis test (Note that data from OECD 306 and Marine Bodis test tests, if available, are preferred over data from the other biodegradability tests listed here).

3. Bioaccumulation
    OECD 305—Bioconcentration: Flow-through Fish Test
    ASTM E1022—Standard Guide for Conducting Bioconcentration Tests with Fishes and Saltwater Bivalve Mollusks
    OECD 107—Partition coefficient (n-octanol/water): Shake Flask Method
    OECD 117—Partition coefficient (n-octanol/water): HPLC Method
    (Note that data from bioconcentration studies, if available, are preferred over data from the partition coefficient studies listed here)

If OSPAR acceptable data, such as those meeting requirements for a formal HOCNF submittal, are available for each component in a product, then the assessment is relatively straight forward, and each component is assigned a Pass or Fail. The product is assigned a Pass if all of the components receive a Pass, and the product is assigned a Fail if at least one of the components receive a Fail. The scoring system is not limited to this embodiment.

Substances found on the "OSPAR List of Substances/Preparations Used and Discharged Offshore which Are Considered to Pose Little or No Risk to the Environment" (PLONOR list), may be designated as such in this section. If all substances in a product are designated PLONOR, then the product is assigned a Pass.

If OSPAR acceptable data are not available, then the available relevant data can be utilized, with professional judgment, to determine the potential for the substance to pass an OSPAR screen. Similar to the hazard assessment process, allowances can be made for read-across data, professional judgment of data from alternate species and test methods, etc. In these cases, substances and products are assigned Provisional Pass or Provisional Fail status.

In the event that neither OSPAR acceptable data, nor data from other reliable sources, are available for a particular endpoint, a "Data Gap" should be assigned. A substance is then assigned a Fail if there are any data gaps. It follows then, that a product will also be assigned a Fail if it comprises one or more substances with data gaps.

An example of an OSPAR Pre-screen is shown in the decision tree illustrated in FIG. 6. The results can be presented in a workbook spreadsheet as shown in FIG. 7. The results of individual tests or protocols are shown and a "substance results" value of pass, fail, provisional pass or provisional fail is provided for each substance or constituent. A "product result" value (e.g., Pass or Fail) is provided base on the results for the constituents, as described above.

In the sixth stage 56, the "Chemical Hazard Evaluation" element is performed to evaluate a substance's intrinsic environmental, toxicological, and physical hazards and provide a quantitative score based on specific endpoints. As discussed above, the Chemical Hazard Evaluation includes three hazard categories, each of which includes selected measurement endpoints that define the specific hazard being evaluated.

In one embodiment, each hazard category includes subcategories having selected measurement endpoints that define the specific hazard being evaluated. Numeric scores may be assigned to each endpoint, based on the severity of the hazard posed by the product, e.g., patterned after the GHS standard. For example, the more hazardous a substance is with respect to a certain endpoint, the higher the score, and vice versa. Exemplary hazard categories include an "environmental" category with measurement endpoints of Acute Aquatic Toxicity, Bioaccumulation and Biodegradation, a "toxicological" category with Acute Mammalian Toxicity, Carcinogenicity, Genetic Toxicity, Reproductive and Developmental Toxicity, and Eye/Skin Corrosive/Irritant endpoints, and a "physical" category with Explosive, Flammable, Oxidizer, and Metal Corrosive endpoints.

Examples of scoring criteria for each endpoint in these subcategories are shown in the following tables:

ACUTE AQUATIC TOXICITY, ACUTE MAMMALIAN TOXICITY, CARCINOGENICITY, AND MUTAGENICITY

3 = Extremely Hazardous or Known to Cause Harm
2 = Moderately Hazardous or Reasonably Anticipated to Cause Harm
1 = Possibly Hazardous or Suspected of Causing Harm
0 = Non-Hazardous or Not Likely to Cause Harm

BIOACCUMULATION

3 = High Potential to Bioaccumulate
2 = Moderate Potential to Bioaccumulate
1 = Possibly Hazardous or Suspected of Causing Harm
0 = Non-Hazardous or Not Likely to Cause Harm

BIODEGRADATION

3 = Not Biodegradable, or produces degradation products of concern
2 = Slightly Biodegradable
1 = Moderately Biodegradable
0 = Readily or Inherently Biodegradable, and does not produce degradation products of concern

EYE & SKIN CORROSIVE/IRRITANT

1 = At Minimum, Possibly Hazardous or Causes Irreversible Effects
0 = Non-Hazardous or Causes Reversible Effects

REPRODUCTIVE AND DEVELOPMENTAL TOXICITY

3 = At Minimum, Possibly Hazardous or Harmful Effects Observed
0 = Non-Hazardous or No Adverse Effects Observed

EXPLOSIVE

3 = GHS Division 1.1 or US DOT Division 1.1
2 = GHS Division 1.2 or US DOT Division 1.2 or 1.3
1 = GHS Division 1.3 or 1.4 or US DOT Division 1.4 or 1.5
0 = GHS Division 1.5 or 1.6 or US DOT Division 1.6

FLAMMABILITY

3 = Flash point <23° C. and initial boiling point ≤35° C.
2 = Flash point <23° C. and initial boiling point >35° C.
1 = Flash point ≥23° C. and ≤60° C.
0 = Flash point >60° C.

Within each of the chemical hazard categories, a score is assigned to each endpoint, based on the severity of potential harm. A score can be calculated, e.g., by summing the scores for each hazard category for each substance or constituent to calculate a total score. The scores may be weighted based on percent composition (by mass) and summed for each component and hazard category in the product. An exemplary scoring system, which is shown in FIG. 8, provides possible scores ranging from zero to 3400. A normalized, relative total score, e.g., ranging from 0 to 100, is also calculated. The normalized score may be calculated by scaling a total score of a substance, product or system to a selected range. The normalized score is calculated, for example, by weighting the score for each substance of a product (or each substance and/or product of a fluid system) based on the proportion of the substance, e.g., the percentage by mass or volume. For example, a normalized score of zero represents the lowest level of hazard and 100 represents the highest level of hazard.

For purposes of data quality and reliability, every effort should be made to obtain a complete as possible product composition, which comprises all known or intentionally added chemical substances in the product being evaluated. Notwithstanding, instances may occur wherein this level of formula detail may not be available. The chemical hazard evaluation is then performed with the best available information. In one embodiment, for purposes of formula quality and reliability, formula composition reported on MSD(S)s are appropriate only in instances wherein all other efforts to obtain complete product composition (including but not limited to Non-Disclosure or Confidentiality Agreements) have been exhausted.

The data used to generate scores may be based either on individual substances of a product or the product blend as a whole, depending upon available information. If data for an entire mixture are available, this data may be used for ranking. When mixture data are used, documentation should be provided in the scoring worksheet with a footnote to the applicable end point(s).

In the event that only ranges are available for product percent composition, in one embodiment, the maximum percent values for each constituent substance are added, and 100 is divided by the total. This calculates a multiplying factor to be applied to the maximum percentage numbers for each of the components. This will allow a conservative number to be used within a 100% constituent framework. For example:

| Component | Minimum % range value | Maximum % range value | Adjustment Factor | Adjusted % composition value |
|---|---|---|---|---|
| A | 20% | 40% | (100/170) = 0.59 | (40 * 0.59) = 23.6% |
| B | 30% | 60% | (100/170) = 0.59 | (60 * 0.59) = 35.4% |
| C | 50% | 70% | (100/170) = 0.59 | (70 * 0.59) = 41.3% |
| Total Percentages | 100% | 170% | | 100% |

When reliable, relevant and adequate data are not available (i.e. a data gap) to assign a score to a given end point, the highest conservative score (e.g., 3) is assigned to the endpoint. The data gap process is described below. For example, for data gaps in reproductive toxicity (normally scored as 0 or 3), a score of 3 should be used. For data gaps in eye and skin corrosive/irritant (normally scored as 0 or 1) a score of 1 should be used. If multiple study results are available then professional judgment or the weight of evidence approach must be considered to determine which values to use for scoring.

The categories and criteria may be based on a single regulatory standard, or be a mixture of categories and criteria from multiple standards. In addition, regulatory standards used in this assessment can be customized as needed to improve efficiency of the assessment.

In one embodiment, categories of GHS are selected for assessment that have applicability to the energy industry. Retaining all hazard categories from the GHS would result in unnecessary complexity without significant improvement in the system to identify hazards intrinsic to oilfield chemicals. For example, hazard categories such as aspiration hazard, respiratory or skin sensitization, self-heating substances and substances that emit flammable gases due to contact with water are excluded from the hazard assessment.

Some hazard categories could be combined to improve efficiency of the assessment process without compromising the assessment. For example, GHS divides oxidizing substances into three categories (solids, liquids and gases), where the present assessment identifies only one category (oxidizing substances).

In addition to the modification of the GHS standard, the assessment may incorporate other sources whose approach follows the spirit of GHS, but provides assessment categories and/or tools more in line with oilfield applications. For example, the criteria for oxidizers in the current assessment are based on the National Fire Protection Association (NFPA) 400/430 list, and the criteria for metal corrosive substances include the US Department of Transportation (DOT) Hazard Class 8, Packing Groups I, II, and III (NFPA 400, NFPA 430 and USDOT, 49 CFR 173.137) The following tables show examples of such categories:

TABLE 12

| OXIDIZER |
|---|
| 3 = NFPA 400/430, Class 3 or 4 |
| 2 = NFPA 400/430, Class 2 |
| 1 = NFPA 400/430, Class 1 |
| 0 = Not listed in NFPA 400/430 |

TABLE 13

| METAL CORROSIVE |
|---|
| 3 = Corrosion rate on either steel or aluminum greater than 6.25 mpy at a test temperature of 55° C., or US DOT Class 8, Packing Group I, II, or III |
| 0 = Corrosion rate on either steel or aluminum less than or equal to 6.25 mpy at a test temperature of 55° C., or US DOT Class 8, unregulated. |

Selecting key hazard classes and customizing these classes and criteria for oilfield application results in an efficient and thorough assessment of oilfield related chemical products.

FIGS. 9-11 show portions of a workbook, e.g., spreadsheets, that illustrate exemplary methods of determining the Chemical Hazard Evaluation criteria measurement endpoints and assigning scores to each criterion. These portions may be part of an output provided to a user, e.g., along with the scoring spreadsheet shown in FIG. 8.

Referring to FIG. 9, the Acute Aquatic Toxicity, Bioaccumulation and Biodegradation scores are assigned, based on available data. For example, Acute toxicity is determined using either a fish 96 hr. LC50, a crustacea 48 hr. LC50, or algal species 72 or 96 hr. EC50 for growth inhibition. When reviewing these data, it is preferred that such data is clearly referenced to a standard test method (i.e. OECD, ISO, ASTM, etc.). For data from non-standard methods, test conditions should be clearly and completely stated. When more than one acceptable toxicity value is available from either the same or a different trophic level, the most conservative (lowest) value may be used. The following criteria are used to assign a score based on acute toxicity data: LC50 or EC50≥100 ppm are scored as 0; LC50 or EC50>10 ppm and ≤100 ppm are scored as 1; LC50 or EC50>1 ppm and <10 ppm are scored as 2; and LC50 or EC50≤1 ppm are scored as 3.

The potential for bioaccumulation is assessed, in one embodiment, using a bioconcentration factor (BCF). Experimentally derived BCF values in fish are ultimately preferred and will override estimated or modeled BCF values. If BCF data are unavailable for fish, data from other species such as mussels, oysters and other mollusks can be used. In the absence of BCF data, studies with bioaccumulation (BAF) data can be used. Octanol/water partition coefficient data (log Pow or log Kow) may be used as an indication of bioaccumulation in the absence of BCF data. Chemical substances with a molecular weight greater than 700 g/mol may be presumed not to pass through cell membranes, are therefore not considered to bioaccumulate, and may be assigned the lowest score (e.g. 1). Using partition coefficient data to assess bioaccumulation for chemical substances which have surface active properties (e.g. surfactants) is not appropriate and, in the absence of BCF data, such substances should be assigned the highest conservative score (e.g. 3).

The following criteria are used to assign scores, based on either BCF or log (Kow) data: BCF values <1000 or log(Kow) values ≤4.0 and molecular weight >700 g/mol are scored as 0; BCF values <2000 and ≥1000 are scored as 1; BCF values <5000 and ≥2000 or log(Kow) values ≥4.0 and molecular weight ≤700 are scored as 2; and BCF values ≥5000 are scored as 3.

Biodegradation is a key parameter for estimating the risk of long-term adverse effects on biota. Ready biodegradation tests are conducted under aerobic conditions, in which a high concentration of the test substance (typically ranging from 2 to 100 mg/L) is used and biodegradation is measured by non-specific parameters like Dissolved Organic Carbon (DOC), Biochemical Oxygen Demand (BOD), and CO2 production. For freshwater tests, domestic sewage, activated sludge, or secondary effluent is the typical source of microorganisms (inoculum). For seawater tests, a variety of indigenous marine microorganisms comprises the inoculum. Quantitative data from the following protocols are acceptable for use in scoring this endpoint: OECD 306, OECD 301 A-F, OECD 302 A-C, or BOD5 test. Note that data from OECD 306 tests, if available, are preferred over data from other biodegradability tests. Biodegradation scores are assigned based on the following: Biodegradation values ≥60%, and if the substance does not produce degradation products of concern, are scored as 0; Biodegradation values <59% and ≥40% are scored as 1; Biodegradation values <39% and ≥20% are scored as 2; and Biodegradation values ≤19%, or if the substance produces degradation products of concern are scored as 3.

Additionally, substances described as "readily biodegradable," are scored as 0. Substances described as "not subject to further degradation in the environment," "persistent" or "not readily biodegradable" should be scored as 3. Biodegradation tests are not applicable to inorganic substances and should be scored as a 0.

FIGS. 10A and 10B illustrate a worksheet that provides criteria for scoring Toxicity of a chemical substance. Toxicity is scored based on acute toxicity values for the substance. The toxicity score, in one example, is based on the three exposure routes identified by GHS, i.e., oral, dermal and inhalation. Inhalation studies using gas, vapor, and dust/mist use different threshold ranges for scoring; it is therefore important to determine the physical properties of the substance used for an inhalation study. If only a single acute toxicology endpoint is available, the overall scoring is based on that single data point. If data are available for more than one exposure route, each should be scored separately and the average taken as the overall score. The scoring can be weighted based on the number of exposure routes as shown in FIG. 10B.

Carcinogenicity may be scored based on various authoritative agency determinations. FIG. 10 shows exemplary substance categorizations for agencies including CLP, IARC, NTP, or EPA, and scores that should be assigned based on categorization. Substances not categorized by these agencies should be scored as 0. In addition, since the assessment is designed to be an assessment of a substance's intrinsic hazards, carcinogens should be scored regardless of whether the designation is limited to a single route of exposure.

Genetic toxicity (mutagenicity) is scored based on the following criteria: Negative results in all mammalian in-vitro or in-vivo tests, or human epidemiological studies, or Ames tests, should be scored as 0; Positive result in all in-vitro somatic cell tests or weight of evidence if more than one Ames test result is reported, should be scored as 1; Evidence for genetic toxicity in mammalian germ cells should be scored as 2; and Evidence of genotoxicity in human epidemiological studies should be scored as 3.

If quantitative positive results of tests for developmental and reproductive toxicity are provided, the substance should be scored as 3. If no information is available for reproductive toxicity, this data-gap should be scored conservatively as 3. If the available data shows no hazard, then the substance should be scored as 0.

If the results of skin corrosivity, skin irritation, or eye irritation studies are available, categories can be established for assignment of an appropriate corrosivity/irritation score. Such categories are shown in FIG. 10B under the heading "Skin and Eye Irritation Effects: Quantitative Descriptions." However, if information regarding irritation and skin corrosivity are provided as descriptive phrases, the guidelines provided under the heading "Skin and Eye Irritation Effects: Quantitative Descriptions" in FIG. 10B, which are based on the Hazard Materials Identification System (HMIS), should be consulted for scoring. In other examples, if the MSDS states that a chemical is an "irritant," it should be given a score of 1.

If the data provided in the MSDS are sufficient in describing the corrosive or irritating properties of a product or substance, the MSDS description may be used for scoring. An example of a sufficient description would be "substance causes burns to skin and eyes" or "substance is moderately irritating." However, if the description of irritant hazards provided is unclear or indicates that the product "can" or "may" cause irritation, this is to be considered a data gap. In this case, database searches should be conducted to find study results to more accurately indicate the irritation hazards of individual substances.

Professional judgment should be used to determine whether the irritant hazard description provided in the MSDS is applicable to the entire product or to the hazardous substances alone. If the MSDS provides definitive effects or study results for mixture data, this information can be used for scoring the entire product. When mixture data are used, one score should be applied to each substance, including non-hazardous substances of the mixture. If the hazard description in the MSDS does not apply to the entire product, each substance should be scored separately.

Referring to FIG. 11, physical hazards can be evaluated and/or scored based on a number of categories. For example, four physical hazard categories (explosive, flammable, corrosive, and oxidizer) are representative of US Department of Transportation (US DOT) hazard classes that should, by law, be designated on the MSDS. Therefore, if a chemical is not specified as explosive, flammable, oxidizing, or corrosive on an MSDS, it should be scored as zero.

For explosive category scoring, the following criteria may be used for scoring:

| | Possible Scores | | | |
|---|---|---|---|---|
| | 0 | 1 | 2 | 3 |
| GHS Classification | Divisions 1.4, 1.5, or 1.6- Substances, mixtures, and articles which pose no significant hazard. | Division 1.3- Combustion of substances, mixtures and articles that gives rise to considerable radiant heat or which burn one after another producing minor blast and/or projection effects. | Division 1.2- Substances, mixtures, and articles which have a fire hazard and either a minor blast and/or projection hazard, but not a mass explosion hazard. | Division 1.1- Substances, mixtures and articles which have as mass explosion hazard |

-continued

| | Possible Scores | | | |
|---|---|---|---|---|
| | 0 | 1 | 2 | 3 |
| USDOT Classification | Division 1.6-Extremely insensitive explosives | Division 1.4-Explosives with a major fire hazard or Division 1.5-Blasting agents. | Division 1.2-Explosives with a blast/projection hazard or Division 1.3-Explosives with a minor blast hazard | Division 1.1-Explosives with a mass explosion hazard |
| IMDG Classification | Division 1.5 or Division 1.6 | Division 1.3 or Division 1.4 | Dvision 1.2 | Division 1.1 |

The following flammability criteria, based on the GHS system, can be used to score flammable products: flash point >60° C. (140° F.) and ≤93° C. (199.4° F.), should be scored as 0; flash point ≥23° C. (73.4° F.) and ≤60° C. (140° F.), should be scored as 1; flash point ≤23° C. (73.4° F.) and initial boiling point >35° C. (95° F.), should be scored as 2; and flash point <23° C. (73.4° F.) and initial boiling point ≤35° C. (95° F.), should be scored as 3.

The following criteria, based on the GHS system, can be used to score corrosive products: Score as 0 if the corrosion rate on either steel or aluminum surfaces <6.25 mm per year (MPY) at a test temperature of 55° C. (131° F.), or MSDS indicates product is US DOT Class 8, unregulated. Score as 3 if the corrosion rate on either steel or aluminum surfaces ≥6.25 mm per year (MPY) at a test temperature of 55° C. (131° F.), or MSDS indicates product is USDOT Class 8, Packing Group I, II, or III.

In the seventh stage 57, the assessment results from each chemical substance are compiled or combined, and provided as an output describing the overall assessment. Accordingly, the assessment results may include any combination of qualitative, quantitative and descriptive information for relative comparison of chemical products.

This report may include one or more numbers, scores, qualitative descriptions, and/or descriptions of the assessment process. For example, the assessment results can be presented in a workbook format including one or more of the worksheets illustrated in FIGS. 4-11. In another example, the assessment results are output (e.g., displayed, printed, etc.) as a report that summarizes each assessment component and provides the results of each component. The report may also summarize and presents the results for a chemical product (comprising a combination of chemical components).

The report may include assessment results for a single chemical substance or multiple chemical substances. In one embodiment, the method includes evaluating potential hazards for one or more individual chemical substances or constituents, a chemical product including multiple constituents, and/or a material or fluid system including multiple chemical products. For example, as shown in FIGS. 5, 7 and 8, the report includes individual assessments for each of a plurality of substances or constituents of a chemical product or fluid/material system. Quantitative scores or other results can be accumulated or otherwise combined to provide a combined score for the product or system based on the individual chemical substance scores. The report may display or otherwise indicate the relative impact score, number or level for each of the substances, products and fluid/material systems.

An exemplary report includes a Highly Discouraged Substances List section that describes the assessment, and indicates whether the chemical product was found in the Highly Discouraged Substances List. If the chemical product was found, the report may include recommendations for replacement. An OSPAR Pre-screen section indicates the result of the Pre-Screen Prediction. A Regulatory Impact Assessment section summarizes the assessment and provides information regarding the potential regulatory impact, e.g., a number and/or list of regulations applicable to the product. A Chemical Hazard Evaluation section provides results of the hazard assessment, may discuss applicable criteria, and may provide a hazard assessment score.

In one embodiment, the various assessments and methods described above include a process for selecting data and data sources and evaluating the quality of such data and data sources. The accuracy of a hazard evaluation for a product is highly dependent on the reliability of data sources. It is important then, to seek out 'definitive' sources, for example, those with data that may be used for regulatory decision making, or sources that also provide study details and metadata. Preferred data is relevant, reliable and sufficient for quantitative purposes. Using reliable data sources increases the likelihood that high quality data will be used to perform chemical assessment.

For example, data from studies conducted under Good Laboratory Practices (GLP) are strongly preferred over non-GLP data. Similarly, data from standardized study protocols (e.g., OECD and USEPA) are preferred over data from tests conducted using non-standard protocols. Finally, Klimisch categories that are routinely assigned to environmental and human health toxicity studies define levels of reliability. For example, in cases where Klimisch scores are reported, only data with Klimisch scores of 1 and 2, i.e., "used without restriction" and "used with restriction" respectively, are sufficient for evaluation.

When encountering multiple and differing data values for a single hazard category or endpoint, it may be necessary to base the assessment on a preponderance of available data, combined with experience and professional judgment. The following are exemplary source categories:

1. The European Chemicals Agency (ECHA) Database of Information on REACH Registered Substances This database contains over 25,000 dossiers on over 4,000 unique substances, and each study contains information that establishes whether data is relevant, reliable, and sufficient for quantitative assessment. This includes study Klimisch scores, GLP status, comparison of the study protocol to established methods, and study details such as number and species of test organisms used, test substance administration and exposure duration, observations, results and discussion.

2. Authoritative Literature and Database Compilations

Several sources make data available, only after it has undergone one or more stages of peer review, by a committee of experienced and specialized scientists. For example, the US National Library of Medicine TOXNET database, the USEPA High Production Volume Program reports, USEPA Pesticide Registration Eligibility Decisions (REDs), Australian National Industrial Chemicals Notification and Assessment Scheme (NICNAS) reports, European Commission Scientific Committee on Consumer Safety (SCCS) opinions, and others were originally published to support regulatory decisions.

3. (Material) Safety Data Sheets

These documents may be used as a data source to address product-level qualities such as physical hazard data and regulatory flags as well as supplier-identified hazards. (M)SDS data, subject to quality on a case-by-case basis, may be useful where hazard and toxicity information is unavailable from a more reliable source, or to corroborate or identify inconsistencies in data obtained from other sources.

4. Data from Read-Across Substances and Mathematical Modeling

Briefly, estimations of toxicity based on QSARs rely on the identification of relationship between chemical structures and biological activity; chemicals with similar structural attributes are inferred to possess similar toxicity. Since qualitative read-across estimations and QSAR models are considered less reliable sources of data, these should be used when all other sources have been exhausted. Data development and interpretation from these sources requires experience and prudent exercise of professional judgment. Some widely used QSAR models include USEPA's EPISuite, Analog Identification Methodology, Interspecies Correlation Estimate, and the OECD QSAR Toolbox.

When all available data are neither relevant nor reliable, nor sufficient for quantitative assessment, or where data is completely lacking, a data gap is noted in the evaluation. The most conservative and protective score possible (i.e., the worst score or score representing the highest hazard level) is assigned to the endpoint until more definitive data can be obtained.

Figure 12:
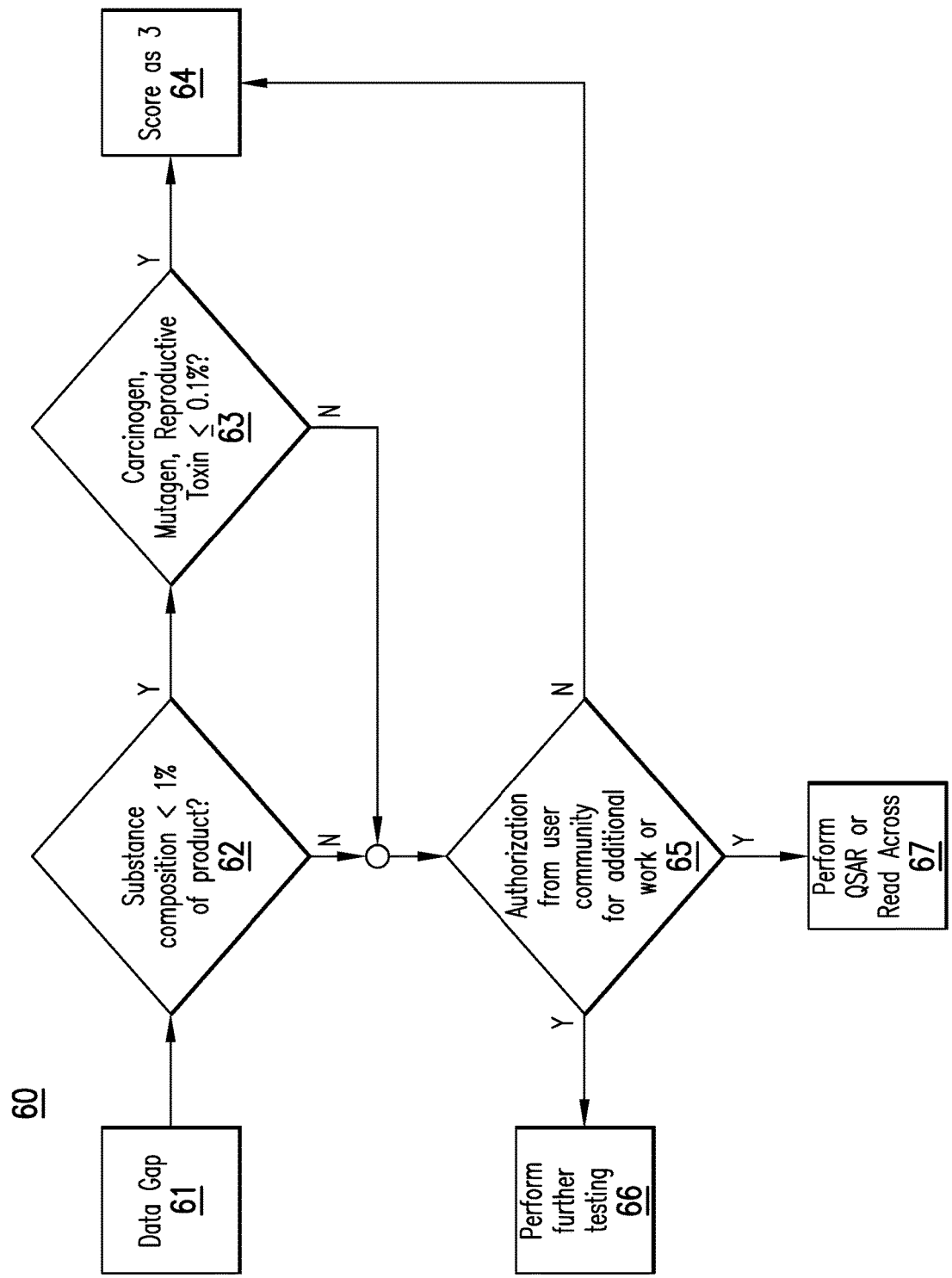
FIG. 12 is a flow chart illustrating an embodiment of a method for evaluating input data gaps.

FIG. 12 illustrates an embodiment of a method 60 for evaluating and using data sources for the chemical assessment described above. In the first block 61, a data gap is identified for a chemical substance that is a constituent of a product. In block 62, the proportion of the product is identified. If the substance is, e.g., <1% of the total product composition and includes either carcinogens, mutagens or reproductive toxins present at ≤0.1% (block 63), it may be assigned the most conservative score, e.g., scored as 3 (block 64). At these concentrations, there is likely no impact to the total hazard score.

For substances with data gaps at higher concentrations, input and discussion from other relevant stakeholders may be consulted at block 65 to determine whether further testing should be performed. This input should consider, among other things, product market potential, impact of the respective substance on overall product performance, and potential costs for additional testing and research. Based on this input, a decision is made whether to proceed with additional testing (block 66) and/or modeling (block 67). If additional work is agreed to, the substance will be scored a 3, until the additional data are made available. If a decision is made to not pursue additional work, the respective substance will be scored a 3.

Figure 15:
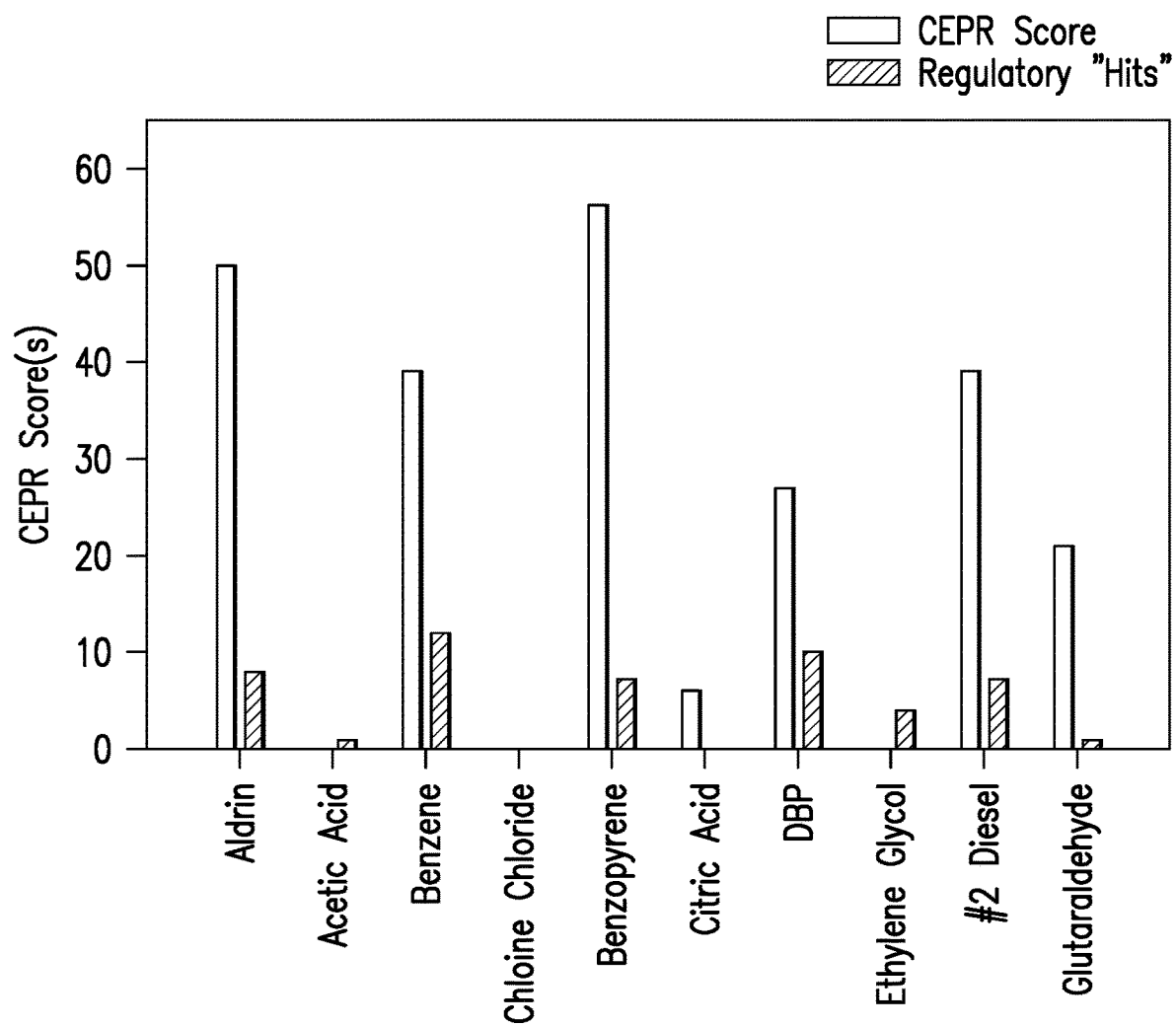
FIG. 15 illustrates a comparison of the chemical assessment results of FIGS. 13 and 14.

FIGS. 13-15 illustrate examples of chemical assessment results generated using the systems and methods described herein. A first group of chemicals (Group 1) were selected and assessed. Group 1 includes aldrin (Chemical Abstracts Service (CAS) No. 309-00-2), benzene (CAS No. 71-43-2), benzo[a]pyrene (50-32-8), dibutylphthalate (84-74-2), and Number 2 Diesel (68476-34-6). A second group of chemicals (Group 2), which are widely used in oilfield or energy industry applications, were also assessed. Group 2 includes acetic acid (64-17-7), choline chloride (67-48-1), citric acid (77-92-9), ethylene glycol (107-21-1) and glutaraldehyde (111-30-8).

FIG. 13 shows the results of the assessment of Group 1. As shown, four of five of the substances evaluated would "Fail" the Pre-Screen Prediction, and all have been assigned at least one Harmonized CLP H-phrase (e.g., may cause genetic defects or cancer). In addition, these substances are highly regulated; the range of regulatory hits ranged from 7 to 12. The total assessment hazard score (CEPR score) ranged from 27 to 56 out of 100.

The results of Group 2, shown in FIG. 14, were much more favorable. All of the substances would "Pass" the Pre-Screen Prediction and none of the substances have been assigned a Harmonized CLP H-phrase. In addition, the substances are not highly regulated. The assessment scores ranged from zero to 21. FIG. 15 shows a comparison of the regulatory count and hazard score of all of the evaluated substances.

One or more aspects of the present invention can be included in an article of manufacture (e.g., one or more computer program products) having, for instance, computer usable media. The media has therein, for instance, computer readable instructions, program code means or logic (e.g., code, commands, etc.) to provide and facilitate the capabilities of the present invention. The article of manufacture can be included as a part of a computer system or provided separately. These instructions may provide for equipment operation, control, data collection and analysis and other functions deemed relevant by a system designer, owner, user or other such personnel, in addition to the functions described in this disclosure.

One example of an article of manufacture or a computer program product for executing the methods described is a processing device or system such as the system 30, the processing unit 32 and/or the host 34. A computer program product includes, for instance, one or more computer usable media to store computer readable program code means or logic thereon to provide and facilitate one or more aspects of the methods and systems described herein. The medium can be an electronic, magnetic, optical, electromagnetic, infrared or semiconductor system (or apparatus or device) or a propagation medium. Example of a computer readable medium include a semiconductor or solid state memory, magnetic tape, a removable computer diskette, a random access memory (RAM), a read-only memory (ROM), a rigid magnetic disk and an optical disk. Examples of optical disks include compact disk-read only memory (CD-ROM), compact disk-read/write (CD-R/W) and DVD.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of assessing chemical products, the method comprising:

receiving input data including identification of a chemical substance at a processing device;

evaluating a regulatory impact of the chemical substance based on at least one of global regulation data, regional regulation data and jurisdiction-specific regulation data, and outputting a regulatory impact assessment, the regulatory impact assessment including a regulatory impact score based on a number of applicable regulations that apply to the chemical substance, the regulatory impact score including a numerical value indicative of the number of applicable regulations;

evaluating potential hazards posed by the chemical substance based on available data related to characteristics of the chemical substance by comparing the characteristics to a plurality of criteria including environmental criteria, toxicity criteria related to effects on human health, and physical criteria related to hazards encountered during material transportation and handling, and outputting a chemical hazard assessment, wherein evaluating the potential hazards includes comparing the characteristics of the chemical substance to selected criteria specified by a pre-existing regulatory chemical evaluation standard for evaluating whether the chemical substance would be accepted for use in a product, and predicting whether the chemical substance would meet the chemical evaluation standard; and generating a chemical assessment report indicating potential impact due to use of the chemical substance, the chemical assessment report indicating chemical assessment results that include the regulatory impact assessment, the regulatory impact score and the chemical hazard assessment, the chemical assessment report including a regulatory impact score, the regulatory impact score based on evaluating the regulatory impact and indicating a level of the regulatory impact.

2. The method of claim 1, wherein the chemical substance is at least a constituent of a chemical product configured for use in an energy industry application.

3. The method of claim 1, further comprising comparing the chemical substance to a list of highly discouraged substances, and including the result of the comparing in the chemical assessment report.

4. The method of claim 1, wherein the chemical evaluation standard is the Oslo-Paris Convention (OSPAR) Harmonized Mandatory Control Scheme (HMCS) Pre-screening scheme, and performing the pre-screen prediction includes at least one of predicting and estimating whether the chemical substance would pass the Pre-screening scheme by comparing the characteristics to a plurality of criteria used by the OSPAR Pre-screening scheme.

5. The method of claim 1, wherein evaluating the regulatory impact includes comparing the chemical substance to substances identified by a plurality of regulatory bodies as requiring regulation, determining the number of applicable regulations based on the comparing, and producing the regulatory impact score based on the number of applicable regulations.

6. The method of claim 1, wherein evaluating potential hazards includes generating a normalized score based on the chemical hazard assessment.

7. The method of claim 1, wherein evaluating potential hazards includes generating scores based on comparison of the characteristics to each of a plurality of criteria, and generating a cumulative chemical hazard score based on the scores.

8. The method of claim 1, further comprising storing the chemical assessment results in a data storage location.

9. The method of claim 8, wherein the chemical substance includes a plurality of chemical constituents, and generating the chemical assessment report includes retrieving the stored chemical assessment results for at least one of the plurality of chemical constituents, and incorporating the stored chemical assessment results into the chemical assessment report.

10. The method of claim 1, wherein the chemical substance is a plurality of chemical substances, the evaluating potential hazards includes evaluating potential hazards of each of the plurality of chemical substances, and the evaluating potential hazards includes at least one of:

evaluating potential hazards of a chemical product, the chemical product including the plurality of chemical substances; and evaluating potential hazards of a fluid system, the fluid system including the plurality of chemical products.

11. The method of claim 10, wherein the chemical assessment report indicates a hazard level for at least one of the chemical substance, the chemical product and the fluid system.

12. A system for assessing chemical products, the system comprising:

a data storage and retrieval device configured to at least one of receive and store source data, the source data including available data related to characteristics of chemical substances and regulatory data including at least one of global regulation data, regional regulation data and jurisdiction-specific regulation data;

a processing device communicatively coupled to the data storage and retrieving device, the processing unit including an input component configured to receive input data including identification of a chemical substance, the processing device configured to perform:

evaluating a regulatory impact of the chemical substance based on the regulatory data, and outputting a regulatory impact assessment, the regulatory impact assessment including a regulatory impact score based on a number of applicable regulations that apply to the chemical substance, the regulatory impact score including a numerical value indicative of the number of applicable regulations;

evaluating potential hazards posed by the chemical substance based on the available data by comparing the characteristics to a plurality of criteria including environmental criteria, toxicity criteria related to effects on human health, and physical criteria related to hazards encountered during material transportation and handling, and outputting a chemical hazard assessment, wherein evaluating the potential hazards includes comparing the characteristics of the chemical substance to selected criteria specified by a pre-existing regulatory chemical evaluation standard for evaluating whether the chemical substance would be accepted for use in a product, and predicting whether the chemical substance would meet the chemical evaluation standard; and generating a chemical assessment report indicating potential impact due to use of the chemical substance, the chemical assessment report indicating chemical assessment results that include the regulatory impact assessment, the regulatory impact score and the chemical hazard assessment, the chemical assessment report including a regulatory impact score, the regulatory impact score based on evaluating the regulatory impact and indicating a level of the regulatory impact.

13. The system of claim 12, wherein the processing unit is configured to perform comparing the chemical substance to a list of highly discouraged substances, and including the result of the comparing in the chemical assessment report.

14. The system of claim 12, wherein the chemical evaluation standard is the Oslo-Paris Convention (OSPAR) Harmonized Mandatory Control Scheme Pre-screening scheme, and the prediction includes at least one of predicting and estimating whether the chemical substance would pass the pre-screening scheme by comparing the characteristics to a plurality of criteria used by the OSPAR pre-screening process.

15. The system of claim 12, wherein evaluating the regulatory impact includes comparing the chemical substance to substances identified by a plurality of regulatory bodies as requiring regulation, and producing the number of applicable regulations, and a list of applicable regulations pertaining to the chemical substance.

16. The system of claim 12, wherein the chemical substance is at least one of a chemical product and a fluid system including a plurality of chemical constituents, and evaluating potential hazards includes generating a score for each of the plurality of constituents, weighting each of the scores based on a proportion of a corresponding constituent in the chemical substance, and combining the weighted scores to generate a combined score for the chemical hazard assessment.

17. The system of claim 12, wherein the processing unit is configured to store the chemical assessment results in a data storage location.

18. The system of claim 17, wherein the chemical substance includes a plurality of chemical constituents, and generating the chemical assessment report includes retrieving the stored chemical assessment results for at least one of the plurality of chemical constituents, and incorporating the stored chemical assessment results into the chemical assessment report.

* * * * *